US005656463A

United States Patent [19]
Slesarev

[11] Patent Number: 5,656,463
[45] Date of Patent: *Aug. 12, 1997

[54] **THERMOSTABLE DNA TOPOISOMERASE V FROM *METHANOPYRUS KANDLERI***

[75] Inventor: Alexei I. Slesarev, Los Angeles, Calif.

[73] Assignee: Fidelity Systems, Inc., Baltimore, Md.

[*] Notice: The term of this patent shall not extend beyond the expiration date of Pat. No. 5,427,928.

[21] Appl. No.: 366,690

[22] Filed: Dec. 30, 1994

Related U.S. Application Data

[63] Continuation-in-part of Ser. No. 38,343, Mar. 24, 1993, Pat. No. 5,427,928.
[51] Int. Cl.$^6$ .................. C12P 19/34; C07H 21/04; C12N 9/90
[52] U.S. Cl. .................. 435/91.5; 435/233; 536/22.1
[58] Field of Search .................. 435/91.5, 233; 536/22.1

[56] References Cited

U.S. PATENT DOCUMENTS

| | | | |
|---|---|---|---|
| 4,894,456 | 1/1990 | Wall et al. | 546/41 |
| 4,963,658 | 10/1990 | Kung et al. | 435/233 |
| 5,070,192 | 12/1991 | Earnshaw et al. | 435/714 |
| 5,106,742 | 4/1992 | Wall et al. | 435/233 |
| 5,122,526 | 6/1992 | Wall et al. | 514/253 |
| 5,244,903 | 9/1993 | Wall et al. | 514/279 |
| 5,427,928 | 6/1995 | Slesarev | 435/91.5 |

FOREIGN PATENT DOCUMENTS

0320308A2  6/1989  European Pat. Off. .

OTHER PUBLICATIONS

J.C. Wang & L.F. Liu, "DNA Replication: Topological Aspects and the Roles of DNA Topoisomerases," in *DNA Topology and Its Biological Effects* (N.R. Cozzarelli & J.C.Wang, eds., Cold Spring Harbor Laboratory Press, Cold Spring Harbor, New York, 1990), Ch. 11, pp. 321–340.

W. M. Huang, "Virus–Encoded DNA Topoisomerases," in *DNA Topology and Its Biological Effects* (N.R. Cozzarelli & J.C. Wang, eds., Cold Spring Harbor Laboratory Press, Cold Spring Harbor, New York, 1990), ch. 9, pp. 265–284.

M.D. Frank–Kamenetskii, "DNA Supercoiling and Unusual Structures," in *DNA Topology and Its Biological Effects* (N.R. Cozzarelli & J.C. Wang, eds., Cold Spring Harbor Laboratory Press, Cold Spring Harbor, New York, 1990), ch. 5, pp. 185–215.

E.C. Lau et al., "Preparation of Denatured Plasmid Templates for PCR Amplification," *Biotechniques* 14:378 (1993).

J. Kato et al., "Purification and Characterization of DNA Topoisomerase IV in *Escherichia coli,*" *J. Biol. Chem.* 267:25676–25684 (1992).

A. Kikuchi et al., "Reverse Gyrase and DNA Supercoiling in Sulfolobus," *System. Appl. Microbiol.* 7:72–78 (1986).

B.S. Glisson & W.E. Ross, "DNA Topoisomerase II: A Primer on the Enzyme and Its Unique Role as a Multidrug Target in Cancer Chemotherapy," *Pharmac. Ther.* 32:89–106 (1987).

P.O. Brown & N.R. Cozzarelli, "A Sign Inversion Mechanism for Enzymatic Supercoiling of DNA," *Science* 206:1081–1083 (1979).

P. Benedetti et al., "The Use of Yeast and Yeast Strains Expressing Human DNA Topoisomerases in the Study of Anticancer Drugs," in *Drug Resistance as a Biochemical Target in Cancer Chemotherapy* (T. Tsuruo & M. Ogawa, eds., Academic Press, San Diego, 1992), ch. 7, pp. 129–145.

P. D'Arpa et al., "Mechanisms of Tumor Cell Killing by Topoisomerase Poisons," in *Drug Resistance as a Biochemical Target in Cancer Chemotherapy* (T. Tsuruo & M. Ogawa, eds., Academic Press, San Diego, 1992) ch. 8, pp. 147–163.

A. L. Bodley, & L. F. Liu, "Topoisomerases as Novel Targets for Cancer Chemotherapy," *Bio/Technology* 6:1315–1319 (1988).

C. Bouthier de la Tour et al., "Reverse Gyrase in Thermophilic Eubacteria," *J. Bact.* 173:3921–3923 (1991).

L. F. Liu, "DNA Topoisomerase Poisons as Antitumor Drugs," *Annu. Rev. Biochem.* 58:351–375 (1989).

S.M. Adams & R. Blakesley, "Linear Amplification DNA Sequencing," *Focus* 13:56–58 (1991).

J.C. Wang, "DNA Topoisomerases," *Annu. Rev. Biochem.* 54:665–697 (1985).

M. Gellert, "DNA Topoisomerases," *Annu. Rev. Biochem.* 50:879–910 (1981).

Y. Zivanovic et al., "Chromatin Reconstitution on Small DNA Rings III. Histone H5 Dependence of DNA Supercoiling in the Nucleosome," *J. Mol. biol.* 214:479–495 (1990).

(List continued on next page.)

*Primary Examiner*—David M. Naff
*Assistant Examiner*—Jon P. Weber
*Attorney, Agent, or Firm*—Merchant, Gould, Smith, Edell, Welter and Schmidt

[57] ABSTRACT

A type 1 topoisomerase, designated topoisomerase V, has been isolated and substantially purified from the halophilic thermophilic methanogen bacterium *Methanopyrus kandleri*. The topoisomerase was purified by a process including the steps of lysing cells of *M. kandleri* to form a lysate, treating the lysate with polyethyleneimine to form a precipitate and a supernatant, precipitating the polyethyleneimine supernatant with ammonium sulfate, chromatographing the ammonium sulfate precipitate on phosphocellulose to produce a phosphocellulose eluate, chromatographing the phosphocellulose eluate on heparin to produce a heparin eluate, and chromatographing the heparin eluate on a column capable separating proteins by molecular size therein to produce a substantially purified thermostable DNA topoisomerase V. Topoisomerase V can relax DNA and can unlink DNA by reducing the linking number of closed circular DNA. Topoisomerase V is active over a wide range of temperatures and ionic conditions and does not require magnesium or ATP for its activity. It is recognized by anti-human topoisomerase I antibody.

6 Claims, 24 Drawing Sheets

OTHER PUBLICATIONS

P. D'Arpa et al., "Use of Molecular Cloning Methods to Map the Distribution of Epitopes on Topoisomerase I (Scl–70) Recognized by Sera of Scleroderma Patients," *Arthritis Rheum.* 33:1501–1511 (1990).

P.F. Agris et al., "Plant DNA Topoisomerase I Is Recognized and Inhibited by Human Scl–70 Sera Autoantibodies," *Exp. Cell Res.* 189:276–279 (1990).

P. Bernard & M. Couturier, "Cell Killing by the F. Plasmid CcdB Protein Involves Poisoning of DNA–Topoisomerase II Complexes," *J. Mol. Biol.* 226:735–745 (1992).

H. Tamura et al., "Molecular Cloning of a cDNA of a Camptothecin–Resistant Human DNA Topoisomerase I and Identification of Mutation Sites," *Nucl. Acids Res.* 19:69–75 (1991).

N. Osheroff, "Biochemical Basis for the Interactions of Type I and Type II Topoisomerases with DNA," *Pharmac. Ther.* 41:223–241 (1989).

P.A. Der Garabedian et al., "$Mg^{2+}$, $Asp^-$, and $Glu^-$ Effects in the Processive and Distributive DNA Relaxation Catalyzed by a Eukaryotic Topoisomerase I," *Biochemistry* 30:9940–9947 (1991).

J. Bashkin et al., "Structure of DNA in a Nucleosome Core at High Salt Concentration and at High Temperature," *Biochemistry* 32:1895–1989 (1993).

R.K. Saiki et al., "Enzymatic Amplication of β–Globin Genomic Sequences and Restriction Site Analysis for Diagnosis of Sickle Cell Anemia," *Science* 230:1350–1354 (1985).

P. D'Arpa et al., "cDNA Cloning of Human DNA Topoisomerase I: Catalytic Activity of a 67.7 kDa Carboxyl–Terminal Fragment," *Proc. Natl. Acad. Sci. USA* 85:2543–2547 (1988).

M.D. Been & J.J. Champoux, "DNA Breakage and Closure by Rat Liver Type I Topoisomerase: Separation of the Half–Reactions by using a Single–Stranded DNA Substrate," *Proc. Natl. Acad. Sci. USA* 78:2883–2887 (1981).

B.F. Pugh et al., "Extent of Duplex DNA Underwinding Induced by RecA Protein Binding in the Presence of ATP," *J. Mol. Biol.* 205:487–492 (1989).

C.A. Parada & K.J. Marians, "Transcriptional Acivation of pBR3422 DNA Can Lead to Duplex DNA Unwinding Catalyzed by the *Escherichia coli* Preprimosome," *J. Biol. Chem.* 264:15120–15129 (1989).

B.F. Pugh and M.M. Cox, "recA Protein Binding to the Heteroduplex Product of DNA Strand Exchange," *J. Biol. Chem.* 262:1337–1343 (1987).

T.A. Baker et al., "Extensive Unwinding of the Plasmid Template During Staged Enzymatic Initiation of DNA replication from the Origin of the *Escherichia coli* Chromosome," *Cell* 45:53–64 (1986).

A.M. Wu et al., "Unwinding Associated with Synapses of DNA Molecules by recA Protein," *Proc. Natl. Acad. Sci. USA* 80:1256–1260 (1983).

U.H. Stettler et al., "Preparation and Characterization of Form V DNA, the Duplex DNA Resulting From Association of Complementary, Circular Single–Stranded DNA," *J. Mol. Biol.* 131:21–40 (1979).

M. Iwabuchi et al., "ATP–Dependent Unwinding of the Double Helix and Extensive Supercoiling by *Escherichia coli* recA Protein in the Presence of Topoisomerase," *J. Biol. Chem.* 258:12394–12404 (1983).

F. Barany, "Genetic Disease Detection and DNA Amplication Using Cloned Thermostable Ligase," *Proc. Natl. Acad. Sci. USA* 88:189–193 (1991).

D. F. Barker, "A More Robust, Rapid Alkaline Denaturation Sequencing Method," *Biotechniques* 14:168–169 (1993).

K. Hsiao, "A Fast and Simple Procedure for Sequencing Double Stranded DNA with Sequenase," *Nucl. Acids Res.* 19:2787 (1991).

G. Pan et al., "Ligation of Synthetic Activated DNA Substrates by Site–Specific Recombinases and Topoisomerase I," *J. Biol. Chem.* 268:3683–3689 (1993).

J.C. Wang, "DNA Topoisomerases," in *Nucleases* (S.M. Linn & R.J. Roberts, eds., Cold Spring Harbor Laboratory Press, Cold Spring Harbor, New York, 1985), pp. 41–57.

R.A. Kim & J.C. Wang, "Identification of the Yeast TOP3 Gene Product as a Single Strand–Specific DNA Topoisomerase," *J. Biol. Chem.* 267:17178–17185 (1992).

J. Siedlecki et al., "Characterization of a Prokaryotic Topoisomerase I Activity in Chloroplast Extracts from Spinach," *Nucl. Acids Res.* 11:1523–1535 (1983).

Y.–H. Hsiang et al., "Camptothecin Induces Protein–Linked DNA Breaks via Mammalian DNA Topoisomerase I," *J. Biol. Chem.* 260:14873–14878 (1985).

A.I. Slesarev et al., "DNA Topoisomerase III From Extremely Thermophilic Archaebacteria," *J. Biol. Chem.* 266:12321–12328 (1991).

G. R. Fink, "A New Twist to the Topoisomerase I Problem," *Cell* 58:225–226 (1989).

A. Young & R. Blakesley, "Sequencing Plasmids from Single Colonies With the dsDNA Cycle Sequencing System," *Focus* 13:137 (1991).

J.C. Wang, "DNA Topoisomerases: Why So Many?" *J. Biol. Chem.* 266:6659–6662 (1991).

K. Drlica & R.J. Franco, "Inhibitors of DNA Topoisomerase," *Biochemistry* 27:2253–2259 (1988).

J.C. Wang et al., "The Role of DNA Topoisomerases in Recombination and Genome Stability: A Double–Edge Sword?" *Cell* 62:403–406 (1990).

A. Maxwell & M. Gellert, "Mechanistic Aspects of DNA Topoisomerases," *Adv. Protein Chem.* 38:69–107 (1986).

T. Hsieh, "Mechanistic Aspects of Type II DNA Topoisomerases," in *DNA Topology and Its Biological Effects* (N.R. Cozzarelli & J.C. Wang, eds., Cold Spring Harbor Laboratory Press, Cold Spring Harbor, New York, 1990), Ch. 7, pp. 243–263.

A. Kikuchi, "Reverse Gyrase and Other Archaebacterial Topoisomerases," in *DNA Topology and Its Biological Effects* (N.R. Cozzarelli & J.C. Wang, eds., Cold Spring Harbor Laboratory Press, Cold Spring Harbor, New York, 1990), ch. 9, pp. 285–298.

D.A. Cowan, "Biotechnology of the Archaea," *TIBTECH* 10: 315–323 (1992).

O.I. Kovalsky et al., "Archaebacterial Reverse Gyrase Cleavage–Site Specificity Is Similar to That of Eubacterial DNA Topoisomerases I," *Nucl. Acids Res.* 18:2801–2805 (1990).

A.I. Slesarev et al., "DNA Topoisomerase V Is a Relative of Eukaryotic Topoisomerase I from a Hyperthermophilic Prokaryote," *Nature* 364: 735–737 (1993).

"Characterization of a Reverse Gyrase from the Extremely Thermophilic Hydrogen–Oxidizing Eubacterium Calderobacterium hydrogenophilum," *FEMS Microbiol. Lett.* 110:107–112 (1993).

C. Bouthier de la Tour et al., "ATP–Independent DNA Topoisomerase from Fervidobacterium islandicum," *Biochim. Biophys. Acta* 1216:213–220 (1993).

K.O. Stetter, "Life at the Upper Temperature Border," in *Colloque Interdisciplinaire du Comite National de la Recherche Scientifique, Frontiers of Life* (J. & K. Tran Thanh Van et al., eds., Editions Frontieres, Gif–Sur–Yvette, France, 1992), pp. 195–219.

D.M. Ward et al., "Ribosomal RNA Analysis of Microorganisms as They Occur in Nature," *Adv. Microb. Ecol.* 12:219–286 (1992).

S.G. Morhan & S. Shuman, "Phenotypic Selection and Characterization of Mutant Alleles of a Eukaryotic DNA Topoisomerase I," *Genes & Development* 4:515–524 (1990).

S.M. Barns et al., "Remarkable Archaeal Diversity Detected in a Yellowstone National Park Hot Springs Environment," *Proc. Natl. Acad. Sci. USA* 91:1609–1613 (1994).

M. Kurr et al., "*Methanopyrus kandleri*, gen. and sp. nov. Represents a Novel Group of Hyperthermophilic Methanogens, Growing at 110 Degrees C," *Arch. Microbiol.* 156:239–247 (1991).

K. Ma et al., "$N^5$, $N^{10}$–Methylenetetrahydromethanopterin Dehydrogenase ($H_2$–Forming) from the Extreme Thermophile *Methanopyrus kandleri*," *Arch. Microbiol.* 156:43–48 (1991).

A. Kikuchi & K. Asai, "Reverse Gyrase—A Topoisomerase Which Introduces Positive Superhelical Turns into DNA," *Nature* 309:677–681 (1984).

W.–K. Eng et al., "Mapping of the Active Site Tyrosine of Eukaryotic DNA Topoisomerase I," *J. Biol. Chem.* 264:13373–13376 (1989).

T. Uemura et al., "Cloning and Sequencing of Schizosaccharomyces pombe DNA Topoisomerase I Gene, and Effect of Gene Disruption," *Nucl. Acids Res.* 15:9727–9739 (1987).

S. Borman, "Bacteria That Flourish Above 100 degrees Celcius Could Benefit Industrial Procressing," *Chem. & Engin. News*, Nov. 4, 1991, pp. 31–34.

S. Burggraf et al., "*Methanopyrus kandleri:*An Archaeal Methanogen Unrelated to All Other Known Methanogens," *Syst. Appl. Microbiol.* 14:346–351 (1991).

R.M. Kelly & J.W. Deming, "Extremely Thermophilic Archaebacteria: Biological and Engineering Considerations," *Biotech. Prog.* 4:47–62 (1988).

A.I. Slesarev et al., "Purification and Characterization of Topoisomerase V," *J. Biol. Chem.* 269:3295–3303 (1994).

Superdex-200a

Superdex-200b

Superdex-200c

Superdex-200d

STRONG TOPO V SITE    ACACTA TAGAATACAAG
                               * *   ** * **
CONSENSUS TOPO I SITE    AGACTT -AGA$^A_G$AAA$^{AAA}_{TTT}$

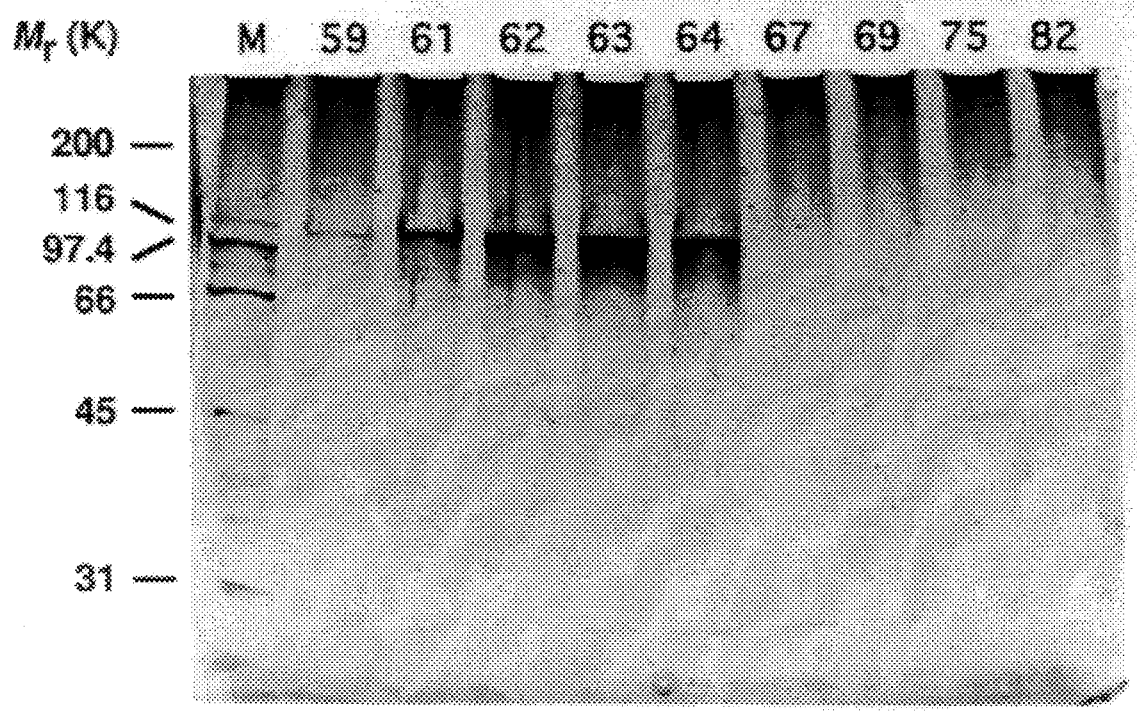

Western blot with anti-human topo I antibodies

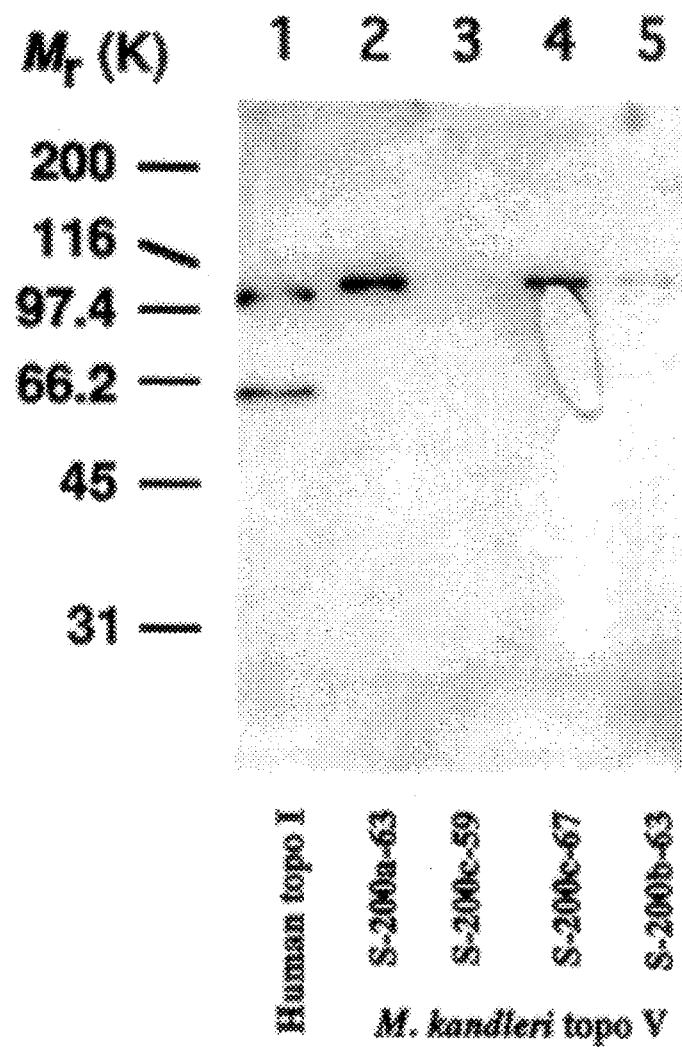

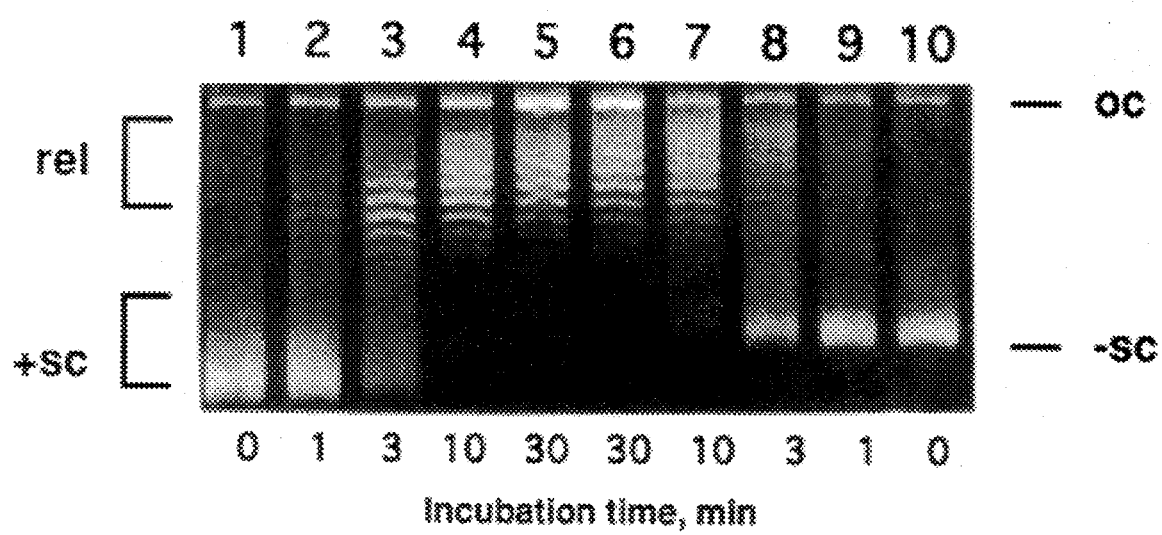

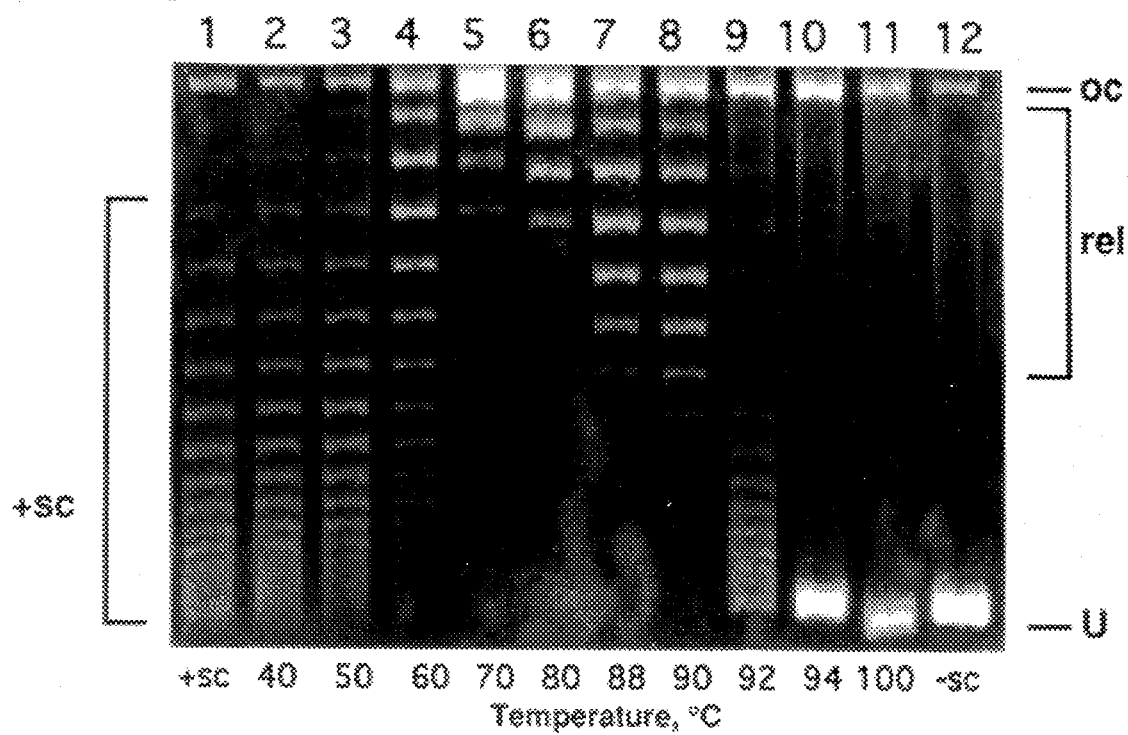

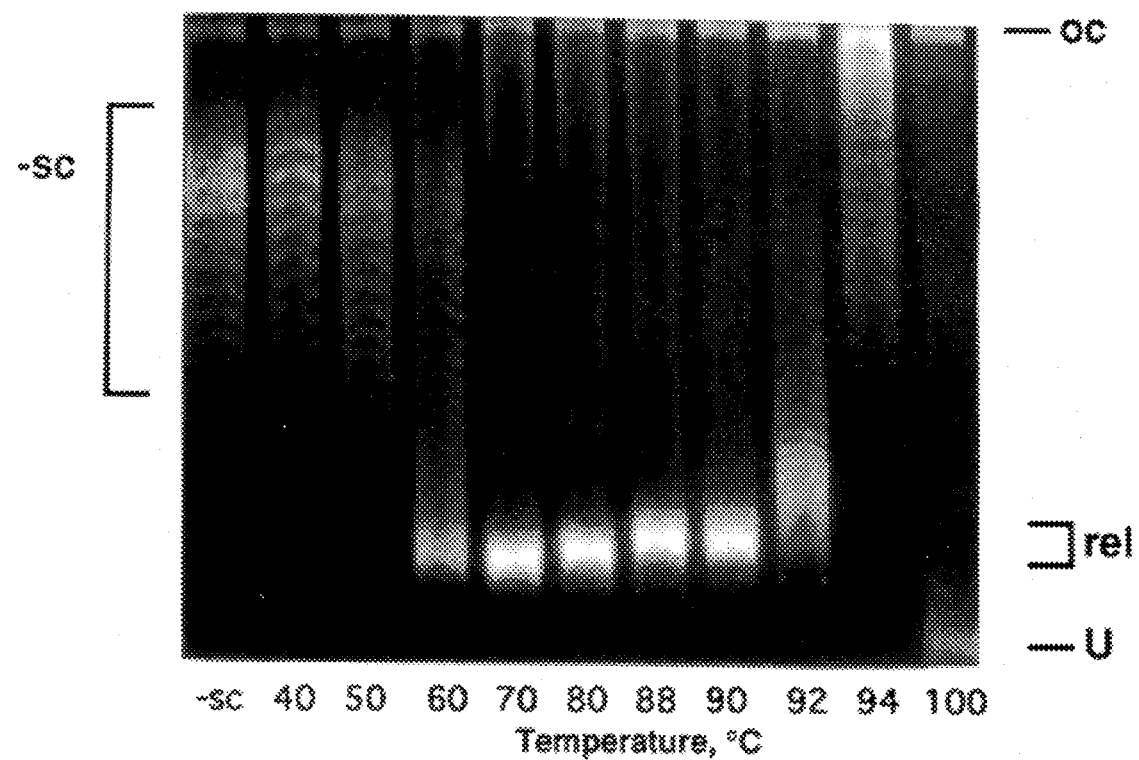

mM K-Glu 5 mM Na$_2$EDTA, 80°C mM K-Glu 5 mM MgCl$_2$, 80°C ss:ds

90°C ss:ds

70°C

THERMOSTABLE DNA TOPOISOMERASE V FROM *METHANOPYRUS KANDLERI*

CROSS-REFERENCE

This application is a continuation-in-part of my prior application Ser. No. 08/038,343, filed Mar. 24, 1993, now U.S. Pat. No. 5,427,928, and also entitled "Thermostable DNA Topoisomerase V from *Methanopyrus kandleri*." The disclosure of that prior application is hereby incorporated herein by reference.

GOVERNMENT RIGHTS

The invention that is the subject of the present application was made while the inventor was associated with the National Institutes of Health. Accordingly, the government may have certain rights in the invention.

BACKGROUND OF THE INVENTION

This invention is directed to a thermostable type I DNA topoisomerase V from the thermophilic prokaryote *Methanopyrus kandleri*, methods for its purification, and methods for its use.

The intertwining of the two strands of the DNA helix presents a number of topological problems which the cell must overcome in order to regenerate, recombine, and express its genetic information (M. Gellert, *Annu. Rev. Biochem.* 50:879–910 (1981); J. C. Wang, *Annu. Rev. Biochem.* 54:665–697 (1985); A. Maxwell and M. Gellert, *Adv. Protein Chem.* 38:68–107 (1986); N. Osheroff, *Pharmac. Ther.* 41: 223–241 (1989); J. C. Wang et al., *Cell* 62:403–406 (1990); J. C. Wang, *J. Biol. Chem.* 266:6659–6662 (1991); A. Kornberg and T. A. Baker, in *DNA Replication* (2d ed.), W. H. Freeman and Company, New York, 1992, pp. 379–401; J. C. Wang and L. F. Liu, in *DNA Topology and Its Biological Effects* (N. R. Cozzarelli and J. C. Wang, eds., Cold Spring Harbor Laboratory Press, New York, 1990, pp. 321–340). Consequently, the enzymes modulating the topological state of nucleic acids, known as DNA topoisomerases, play a crucial role in controlling the physiological functions of DNA.

To simplify the later description, a few definitions relevant to DNA topology are useful. Supercoiling is typical in closed circular DNA (ccDNA) because of the topological linkage of the two complementary strands. The linking number, Lk, is the quantitative measure of this linkage: it is the algebraic number of times one strand crosses the surface stretched over the other strand. The Lk value is a topological invariant for ccDNA; there is no way it can be changed without introducing chain scissions. The number of supercoils can be defined as $$\Delta Lk = Lk - N/\gamma_o$$

where N is the number of base pairs in a DNA and $\gamma_o$ is the number of base pairs per turn of the double helix under given ambient conditions. Specific linking difference, or superhelical density, is defined as $$\sigma = \gamma_o \Delta Lk/N$$

If $\Delta Lk > 0$, DNA is called positively supercoiled; if $\Delta Lk < 0$, DNA is negatively supercoiled. A consequence of negative supercoiling is that the DNA helix is more easily unwound, i.e., the strands are more readily separated, whereas positive supercoiling, by tightening the pitch of the helix, would make unwinding more difficult.

Any changes in the Lk value are resolved into its two geometrical components (J. H. White, *Am. J. Math.* 91: 693–728 (1969))

$$\Delta Lk = \Delta Tw + Wr$$

where $\Delta Tw$ is the difference in the axial twist of either strand about the axis of the double helix, Wr is the quantity related to supercoiling and is determined by the spatial shape of the axis of the double helix (for detailed discussions on general aspect of DNA topology, see *DNA Topology and Its Biological Effects* (N. R. Cozzarelli and J. C. Wang, eds., Cold Spring Harbor Laboratory Press, New York, 1990)).

DNA transformations performed by DNA topoisomerases are accomplished by the cleavage of either a single strand or both strands. The unit change in the Lk upon such transformations is the best operational distinction between the two classes of topoisomerases (P.O. Brown & N. R. Cozzarelli, *Science* 206:1081–1083 (1979)). DNA topoisomerases whose reactions proceed via a transient single-stranded break and changing the Lk in steps of one are classified as type 1, while enzymes whose reactions proceed via double-stranded breaks and changing the Lk in steps of two are classified as type 2.

Members of type 2 topoisomerase family include DNA gyrase, bacterial DNA topoisomerase IV, T-even phage DNA topoisomerases, eukaryotic DNA topoisomerase II, and thermophilic topoisomerase II from *Sulfolobus acidocaldarius* (see reviews cited above; A. Kikuchi et al., *Syst. Appl. Microbiol.* 7:72–78 (1986); J. Kato et al., *J. Biol. Chem.* 267:25676–25684 (1992); W. M. Huang in *DNA Topology and Its Biological Effects* (N. R. Cozzarelli and J. C. Wang, eds., Cold Spring Harbor Laboratory Press, New York, 1990), pp.265–284; T.-S Hsieh in *DNA Topology and Its Biological Effects* (N. R. Cozzarelli and J. C. Wang, eds., Cold Spring Harbor Laboratory Press, New York, 1990), pp.243–263)). The coding sequences of a dozen or so type 2 enzymes have been determined, and the data suggest that all these enzymes are evolutionarily and structurally related. Topological reactions catalyzed by type 2 topoisomerases include introduction of negative supercoils into DNA (DNA gyrase), relaxation of supercoiled DNA, catenation (or decatenation) of duplex circles, knotting and unknotting of DNA.

The family of type 1 topoisomerases comprises bacterial topoisomerase I, *E. coli* topoisomerase III, *S. cerevisiae* topoisomerase III (R. A. Kim & J. C. Wang, *J. Biol. Chem.* 267:17178–17185 (1992)), the type 1 topoisomerase from chloroplasts that closely resembles bacterial enzymes (J. Siedlecki et al., *Nucleic Acids Res.* 11:1523–1536 (1983)), thermophilic reverse gyrases (A. Kikuchi in *DNA Topology and Its Biological Effects* (N. R. Cozzarelli and J. C. Wang, eds., Cold Spring Harbor Laboratory Press, New York, 1990), pp.285–298); C. Boutbier de la Tour et al. *J. Bact.* 173:3921–3923 (1991)), thermophilic *D. amylolyticus* topoisomerase III (A. I. Slesarev et al., *J. Biol. Chem.* 266: 12321–12328 (1991), nuclear topoisomerases I and closely related enzymes from mitochondria and poxviruses (N. Osheroff, *Pharmac. Ther.* 41:223–241 (1989)). With respect to the mechanism of catalysis these topoisomerases can be divided into two groups. Group A consists of enzymes that are single-strand-specific, require a divalent cation for activity, and form a transient covalent complex with the 5'-phosphoryl termini (prokaryotic type 1 topoisomerases and *S. cerevisiae* topoisomerase III). Group B includes type 1 topoisomerases that operate on duplex DNAs, do not require a divalent cation for activity, and bind covalently to the 3'-phosphoryl termini (nuclear topoisomerases I, enzymes from mitochondria and poxviruses commonly called eukaryotic topoisomerases I). Type 1 topoisomerases can carry out the following topological reactions; they relax supercoiled DNA (except of reverse gyrases), catenate (or decatenate) single-stranded circular DNAs or duplexes providing that at least one of the molecules contains a nick or gap, interact with single-stranded circles to introduce topological knots (type 1-group A topoisomerases). Reverse gyrase, belonging to type 1-group A topoisomerases, is the only topoisomerase shown to be able to introduce positive supercoils into ccDNA.

Research on DNA topoisomerases has progressed from DNA enzymology into developmental therapeutics. Bacterial DNA topoisomerase II is an important therapeutic target of quinolone antibiotics; mammalian DNA topoisomerase II is the cellular target of many potent antitumor drugs (K. Drlica, *Microbiol. Rev.* 48:273–289 (1984) and *Biochemistry* 27: 2253–2259 (1988); B. S. Glisson & W. E. Ross, *Pharmacol. Ther.* 32:89–106 (1987); A. L. Bodley & L. F. Liu, *Biotechnology* 6: 1315–1319 (1988); L. F. Liu, *Annu. Rev. Biochem.* 58:351–375 (1989)). These drugs, referred to as topoisomerase II poisons, interfere with the breakage-rejoining reaction of type II topoisomerases by trapping a key covalent reaction intermediate, termed the cleavable complex. Mammalian type 1-group B topoisomerase has been shown to be the target of camptothecin (CPT), a plant alkaloid with strong antitumor activity. CPT and its derivatives also trap a putative covalent reaction intermediate, the clearable complex. This type of reversible DNA damage is lethal to proliferating cells and is responsible for the antitumor activity of topoisomerase poisons (Y.-H. Hsiang et al., *J. Biol. Chem.* 260:14873–14878 (1985); Y. Hsiang et al., *Cancer Res.* 49: 5077–5082 (1989); C. Holm et al., *Cancer Res.* 49:6365–6368 (1989), P. D'Arpa et al. *Cancer Res.* 50:6919–6924 (1990); A. Y. Chen et al. *Cancer Res.* 51:6039–6044 (1991)). Increased attention to CPT and its derivatives as the most promising anticancer agents currently in clinical trials (W. J. Slichenmyer et al., *J. Natl. Cancer Inst.* 85:271–287 (1993); U.S. Pat. No. 5,106,742 (camptothecin analogues as potent inhibitors of topoisomerase I); U.S. Pat. No. 5,122,526 (camptothecin and analogues thereof and pharmaceutical compositions and method using them)) resulted in isolation several CPT-resistant cell lines and a CPT-resistant mutant of human topoisomerase I has been characterized (H. Tamura et al., *Nucleic Acids Res.* 19:69–75 (1991)). Through the use of a yeast strain in which yeast type 1-group B topoisomerase is replaced by its human counterpart, other CPT-resistant mutants of the human enzyme have been isolated (P. Benedetti et al., in *Drug Resistance as a Biochemical Target in Cancer Chemotherapy* (T. Tsuruo, M. Ogawa, & S. K. Carter, eds., Academic Press, San Diego, Calif., 129, 1991)). Further identification of the mutation sites of CPT-resistant type 1-group B topoisomerases is potentially useful for modeling novel derivatives acting against CPT-resistant tumor cells.

To date type 1-group B topoisomerases have been found only in eukaryotes. One might expect that the finding of a prokaryotic counterparts to eukaryotic type 1-group B topoisomerases would be viewed with great interest by pharmacologists and clinicians as well. Whereas it would be important to exploit the common features of type 1-group B topoisomerases, it would be equally important to exploit the differences among them for modeling novel drugs. Also the new organisms harboring type 1-group B topoisomerases would be of clinical interest as potential sources of the natural inhibitors of those enzymes. For example, in *E. coli*, the miniF plasmid CcdB protein, like quinolone antibiotics and antitumoral drugs, promotes DNA gyrase-mediated double-stranded DNA breakage (P. Bernard & M. Couturier, *J. Mol. Biol.* 226:735–745 (1992)).

Another aspect of medical utility of type 1-group B topoisomerases is the identification of the human Scl-70 antigen as DNA topoisomerase I. Scleroderma (progressive systemic sclerosis) patients may produce high titer autoimmune antibody directed against human topoisomerase I (J. H. Shero et al., *Science* 231:737–740 (1986)). The availability of cloned human topoisomerase I enables the development of methods for rapid screening for the presence of these autoantibody in patient sera (P. D'Arpa et al. *Proc. Natl. Acad. Sci. USA* 85:2543–2547 (1988); U.S. Pat. No. 5,070,192 (cloned human topoisomerase I: cDNA expression and use for autoantibody detection)). Remarkably, type 1-group B topoisomerases of higher plants are recognized by human anti-topoisomerase autoantibody, despite the divergence of the kingdoms (P. F. Agris et al., *Exp. Cell Res.*189:276–279 (1990)). It is conceivable that human autoantibody could recognize type 1-group B topoisomerases from prokaryotic organisms as well. Using human antibody on prokaryotic systems immunoprecipitations, competitive binding assays, cellular function studies, and probing expression libraries could be accomplished. The use of human anti-topoisomerase antibody as probes of prokaryotic type 1-group B topoisomerase structure may be important in further understanding the interaction of human topoisomerase I and cancer chemotherapeutic agents. Finally, such cross-reactivity would have clinical significance for autoimmunity as well. Sera of scleroderma patients targeted at least 6 independent epitopes on human topoisomerase I. Molecules of cDNA comprising a part of the cDNA sequence of human topoisomerase I which encode at least one epitope for autoantibody to human topoisomerase I are available (P. D'Arpa et al., *Arthritis Rheum.* 33:1501–1511 (1990)). Other type 1-group B topoisomerases reacting with anti-human topoisomerase I antibody could be used in the same way. It would be important in tracking the emergence of autoimmune antibody against particular epitopes during the progression of disease.

One of the driving forces behind molecular biology is the successful utilization of enzymes as reagents. Mesophilic type 1-group B topoisomerases are widely used for analysis of DNA supercoiling, DNA conformation, transcription in vitro, and chromatin reconstitution (M. D. Frank-Kamenetskii, in *DNA Topology and Its Biological Effects* (N. R. Cozzarelli and J. C. Wang, eds., Cold Spring Harbor Laboratory Press, New York, 1990), pp.185–215; Y. Zivanovic et al., *J. Mol. Biol.* 214:479–495)). The availability of thermophilic type 1-group B topoisomerases simplifies significantly the manipulation of DNA conformation. Reverse gyrase is becoming an indispensable tool for preparation of positively supercoiled DNA, while *D. amylolyticus* topoisomerase III is a convenient tool for preparation of ccDNA with different degree of negative supercoiling (A. I. Slesarev et al. *J. Biol. Chem.* 266: 12321–12328 (1991)).

Chromatin reconstitution in vitro is usually done at 0.5–1.0 M while eukaryotic topoisomerase I is inhibited by 0.2 M and higher concentration of NaCl (P. A. Der Garabedian et al., *Biochemistry* 30:9940–9947 (1990)). At 0.2 M NaCl nucleosome assembly is very inefficient, so there is a need in topoisomerase working in a wide range of ionic strength. Moreover, recent progress in this field increases the need for thermostable topoisomerases with properties akin to those of eukaryotic topoisomerase I (J. Bashkin et al. *Biochemistry*, 32:1895–1898 (1993)).

Other applications of topoisomerases may exploit their ability to cleave DNA at specific sites ("specific endonucleases"), their ability form a covalent complex with DNA, their substrate selectivity. Of potential interest is a topoisomerase religation half-reaction. Type 1-group B topoisomerases catalyze the in vitro ligation of nonhomologous DNA fragments lacking any sequence homology or complementarity (M. D. Been & J. J. Champoux, *Proc. Natl. Acad. Sci. USA* 78:2883–2887 (1981)). Pan et al. disclosed a method for ligation of artificial substrates that bear a tyrosine residue on the 3'-PO$_4$ of an appropriate oligonucleotide with mammalian topoisomerase I (*J. Biol. Chem.* 268:3683–3689 (1993)).

Preparation and analysis of specific nucleotide and protein sequences constitutes a basis of current molecular biology, biotechnology, and molecular medicine. Enzymatic DNA sequencing (F. Sanger, *Proc. Natl. Acad. Sci. USA* 74: 5463–5467 (1977)) using Sequenase enzyme (US Biochemical, Cleveland, Ohio) is currently the most popular method to obtain genetic information. Any improvement in the procedure that will eliminate labor-consuming steps or increase sensitivity, is of great demand in the field. It is generally accepted that, despite problems with DNA denaturation and reassociation, the use of double-stranded DNA for sequencing is preferable to the construction and use of single-stranded DNA. The denaturation of conventionally purified ccDNA involves alkali treatment that is hazardous for DNA followed by time and labor-consuming DNA precipitation, during which reassociation can occur (S. M. Adams et al. *Focus* 13:56–58 (1991); D. F. Barker, *Biotechniques* 14:168–169 (1993)). This results in fewer readable bases. Sequencing at higher temperatures can eliminate reassociation, but results in a higher error rate.

Thus, there is a need for a reliable technology of plasmid template preparation for sequencing compatible with popular sequencing protocols.

Polymerase chain reaction (R. K. Saiki et al., *Science* 230:1350–1354 (1985); H. A. Erlich, ed., *PCR technology: Principles and applications for DNA amplification* (Stockton Press, New York, 1989)) is the basic technique that allows amplification of pieces of DNA starting from tiny amounts of material with limited knowledge about its exact primary structure. Its development and refinement continue at a rapid pace. Another chain reaction introduced in 1990 (European Patent Application EP 88311741.8; F. Barany, *Proc. Natl. Acad. Sci. USA* 88:189–193 (1990)) is based on ligase and is becoming a powerful tool in medical diagnostics. The success of these techniques was due to the use of thermostable enzymes. However, when PCR or LCR amplification is performed on a plasmid template, poor denaturation of ccDNA may result in a failure to detect products (E. C. Lau et al., *Biotechniques* 14:378 (1993)). Therefore, these techniques also need a procedure of plasmid template preparation for reliable primer annealing.

One of the solutions of the above problem consists in the substitution of DNA denaturation with a special and simple topological treatment with a thermostable enzyme(s) that will allow a primer to anneal to the double-stranded DNA with same efficiency as to the single-stranded DNA. The effect is based on the topological destabilization (unlinking) of the double helix that can be varied in a wide range. The limit products of the unlinking are ccDNA with a few links or even single-stranded complementary rings. Such DNA, called form V, can contain 10 to 40% single-stranded regions at room temperature and will melt easily at elevated temperature (U. H. Stettler et al., *J. Mol. Biol.* 131:21–40 (1979)). The non-template strand of the duplex will not hinder subsequent elongation and moreover it will create a topological force in favor of elongation. The method is equally applicable to any procedure that involve primer annealing and/or elongation, i.e., enzymatic ccDNA sequencing, PCR, LCR, hybridization probe preparation, etc.

There are several enzymatic procedures for preparation of highly underwound ccDNA molecules (M. Iwabuchi et al., *J. Biol. Chem.* 258:12394–12404 (1983); A. M. Wu et al., *Proc. Natl. Acad. Sci. USA* 80:1256–1260 (1983); T. A. Baker et al., *Cell* 45:53–64 (1986); B. F. Pugh & M. M. Cox, *J. Biol. Chem.* 262:1326–1336 and 1337–1343 (1987); C. A. Parada & K. J. Marians, *J. Biol. Chem.* 264: 15120–15129 (1989); B. F. Pugh et al., *J. Mol. Biol.* 205: 487–492 (1989)). However, the procedures require multienzyme complexes of at least two different enzymes and specific buffer conditions. In addition, the enzymes used in the above procedures are thermolabile and can not be used in PCR or LCR.

Slesarev et al. disclosed that thermostable type 1-group A topoisomerase III from *Desulfurococcus amylolyticus* can alone substantially reduce the Lk value of ccDNA and generate highly unwound forms of ccDNA in the linear DNA melting range (*J. Biol. Chem.* 266:12321–12328 (1991)). However, this topoisomerase is $Mg^{2+}$-dependent, ineffective at low salt conditions, and inhibited by single-stranded DNA. In addition, it needs very high temperature to be active on relaxed and positively supercoiled DNA. These properties of Dam topoisomerase III will interfere with the standard buffer conditions used in enzymatic DNA sequencing, PCR or LCR and enzyme will be inhibited by the reaction products.

Thus, there is a need for a thermostable (ATP, $Mg^{2+}$)-independent relaxing DNA topoisomerase that is not inhibited by single-stranded DNA, equally active on positively and negatively supercoiled DNA, active through a wide range of temperatures and a wide range of salt conditions, to allow the performance of these manipulations on DNA more conveniently and more efficiently.

SUMMARY

A thermostable type 1-group B DNA topoisomerase has been isolated and purified to substantial homogeneity from the hyperthermophilic methanogen *Methanopyrus kandleri*. This topoisomerase, designated topoisomerase V, is the first type 1-group B topoisomerase known from a prokaryote. The substantially purified topoisomerase is substantially free of other enzymes acting on DNA. The purified topoisomerase is a single chain polypeptide with an estimated molecular mass of about 110,000 daltons, based on sodium dodecyl sulfate-polyacrylamide gel electrophoresis.

Another aspect of the invention is a process for purifying thermostable topoisomerase V. The process comprises:

(1) lysing cells of M. kandleri to form a lysate;

(2) treating the lysate with polyethyleneimine to form a precipitate and a supernatant;

(3) precipitating the polyethyleneimine supernatant with ammonium sulfate;

(4) chromatographing the ammonium sulfate precipitate on phosphocellulose to produce a phosphocellulose eluate;

(5) chromatographing the phosphocellulose eluate on heparin to produce a heparin eluate; and (6) chromatographing the heparin eluate on a column capable of separating proteins by molecular size therein to produce a substantially purified thermostable DNA topoisomerase V.

Another aspect of the invention is a method of relaxation of supercoiled DNA comprising treating a supercoiled DNA selected from the group consisting of positively supercoiled DNA and negatively supercoiled DNA with the topoisomerase of the present invention at a temperature and ionic conditions at which the separation of complementary strands of the linear form of treated closed circular DNA does not occur and at a temperature and ionic conditions that allow the enzyme to bind to DNA and catalyze the relaxation reaction to produce relaxed DNA.

Yet another aspect of the invention is a method of unlinking closed circular DNA comprising treating closed circular DNA with the topoisomerase of the present invention at a temperature and ionic conditions allowing separation of complementary DNA strands of the linear form of treated closed circular DNA and at a temperature and ionic conditions that allow the enzyme to bind to DNA and catalyze the unlinking reaction to produce DNA with a linking number lower than the linking number of the DNA before treatment.

Another aspect of the invention is a complex comprising the topoisomerase of the present invention non-covalently bound to DNA.

Still another aspect of the invention is a complex comprising the topoisomerase of the present invention covalently linked to the 3'-end of a DNA strand. The topoisomerase can be covalently linked to the 3'-end of a broken strand of open circular DNA.

Another aspect of the invention is a method for covalent complex formation comprising:

(1) incubating the topoisomerase of the present invention with DNA under ionic conditions allowing the binding of the topoisomerase to the DNA and the breaking of one strand by the topoisomerase; and (2) denaturing of the topoisomerase leaving a covalent complex between the topoisomerase and the DNA.

Yet another aspect of the invention is a method for use of topoisomerase V of the present invention as a specific endonuclease comprising:

(1) incubating the topoisomerase of the present invention with DNA under ionic conditions allowing the binding of the topoisomerase to the DNA and the breaking of one strand by the topoisomerase at a specific sequence; and (2) then denaturing the topoisomerase yielding cleaved DNA.

Another aspect of the invention is a method for producing an activated DNA substrate with at least a single amino acid residue covalently bound to the 3'-$PO_4$ terminus of a DNA strand adjacent to the recognition site of the topoisomerase of the present invention, comprising:

(1) incubating the topoisomerase with DNA under ionic conditions allowing the binding of the topoisomerase to DNA and the breaking of one strand by the topoisomerase at a specific sequence; and (2) then denaturing the topoisomerase and hydrolyzing the topoisomerase with a nonspecific protease.

Partial amino acid sequences are known for topoisomerase V, including the amino-terminal amino acid sequence and sequences of fragments produced by the proteolytic enzyme endoproteinase Lys-C. Accordingly, also within the scope of the invention are thermophilic type 1-group B DNA topoisomerases active at a temperature of at least 50° C. and possessing an amino-terminal amino acid sequence selected from the group consisting of:

(1) the amino-terminal amino acid sequence of *M. kandleri* topoisomerase V; and (2) an amino-terminal amino acid sequence related to the amino-terminal amino acid sequence of *M. kandleri* topoisomerase V by one or more conservative amino acid substitutions. The topoisomerase is magnesium independent, relaxes both negatively and positively supercoiled DNA, makes a covalent complex with the 3'-end of the broken DNA strand, and cleaves DNA at the third adenosine residue in the sequence A-C-A-C-T-A-T-A-G-A-A-T-A-C-A-A-G (SEQ ID NO: 4).

The amino-terminal amino acid sequence of *M. kadleri* topoisomerase V Ala-Leu-Val-Tyr-Asp-Ala-Glu-Phe-Val-Gly-Ser-Glu-Arg-Glu-Phe-Glu-Glu-Arg-Glu-Thr-Phe-Leu-Lys-Gly-Val-Lys-Ala-Tyr-Asp-Gly-Val-Leu-Ala-Thr-Arg-Tyr-Arg-Tyr-Leu-Met-Glu-Arg-Ser-Ser-Ser-Ala is (SEQ ID NO: 3).

Similarly, within the scope of the invention are thermostable type 1-group B DNA topoisomerases possessing at least one amino acid sequence selected from the group consisting of:

(1) the sequence Lys-Ser-Gly-Arg-Gln-Glu-Arg-Ser-Glu-Glu-Glu-Trp-Lys-Glu-Trp-Leu-Glu-Arg-Lys-Val-Gly-Glu-Gly-Arg-Ala-Arg-Arg-Leu-Ile-Glu-Tyr-Phe-Gly-Ser-Ala (SEQ ID NO: 1)

(2) the sequence Lys-Tyr-Gly-Ser-Ala-Ser-Ala-Val-Arg-Arg-Leu-pro-Val-Glu-Glu-Leu-Arg-Glu-Leu-Gly-Phe-Ser-Asp-Asp-Glu (SEQ ID NO: 2); and (3) a sequence related to the sequences recited in (1)–(2) by one or more conservative amino acid substitutions. The topoisomerase is magnesium independent, relaxes both negatively and positively supercoiled DNA, makes a covalent complex with the 3'-end of the broken DNA strand, and cleaves DNA at the third adenosine residue in the sequence A-C-A-C-T-A-T-A-G-A-A-T-A-C-A-A-G (SEQ ID NO: 4).

Another aspect of the present invention is antibody specifically binding the substantially purified thermostable DNA topoisomerase of the present invention. The antibody can be a monoclonal antibody.

Another aspect of the invention is an immunoreactive complex of topoisomerase V of the present invention with anti-human topoisomerase I antibody.

Another aspect of the invention is an immunoassay for the detection or determination of the topoisomerase of the present invention with anti-human topoisomerase I antibody comprising the steps of:

(1) reacting the topoisomerase with anti-human topoisomerase I antibody; and (2) detecting and/or determining the topoisomerase V by detecting and/Or determining an antigen-antibody complex between the topoisomerase and the antibody.

Other antibodies are also aspects of the present invention. They include: (1) antibody specifically binding a fragment of about 75,000 daltons of the substantially purified topoisomerase of the present invention originating from the amino-terminus of the topoisomerase protein; and (2) antibody specifically binding a fragment of about 33,000 daltons of the substantially purified topoisomerase of the present invention originating from the carboxyl-terminus of the topoisomerase protein.

BRIEF DESCRIPTION OF THE DRAWINGS

These and other features, aspects and advantages of the present invention will become better understood with reference to the following description, appended claims, and the accompanying drawings where:

FIG. 5B is a photograph of a silver-stained 7.5% polyacrylamide gel showing the protein composition of fractions from the eluate resulting from gel filtration of fraction Va, showing additional fractions;

FIG. 7 is an immunoblot of human topoisomerase I, fraction 63 from the gel filtration of fraction Va (S-200a-63), fractions 59 and 67 from the gel filtration of fraction Vc (S-200c-59 and S-200c-67), and fraction 63 from the gel filtration of fraction Vb (S-200b-63);

FIG. 8A is a photograph of an agarose gel showing the time course of the M. kandleri topoisomerase V activity, with positively or negatively supercoiled pBR322 DNA in 30 mM Tris-HCl, pH 8.0 (at 25° C.), 1 M potassium glutamate, and 5 mM Na$_2$EDTA, with electrophoresis in the presence of 1.6 µg/ml chloroquine;

FIG. 8B is a photograph of an agarose gel showing the effect of temperature on the enzymatic activity of M. kandleri topoisomerase V with positively supercoiled pBR322 DNA as substrate in 30 mM Tris-HCl, pH 8.0 (at 25° C.), 1 M potassium glutamate, and 5 mM Na$_2$EDTA;

FIG. 8C is a photograph of an agarose gel showing the effect of temperature on the enzymatic activity of M. kandleri topoisomerase V with negatively supercoiled pBR322 DNA as substrate in 30 mM Tris-HCl, pH 8.0 (at 25° C.), 1 M potassium glutamate, and 5 mM Na$_2$EDTA, with electrophoresis in the presence of 25 µg/ml chloroquine;

DESCRIPTION

Figure 1A:
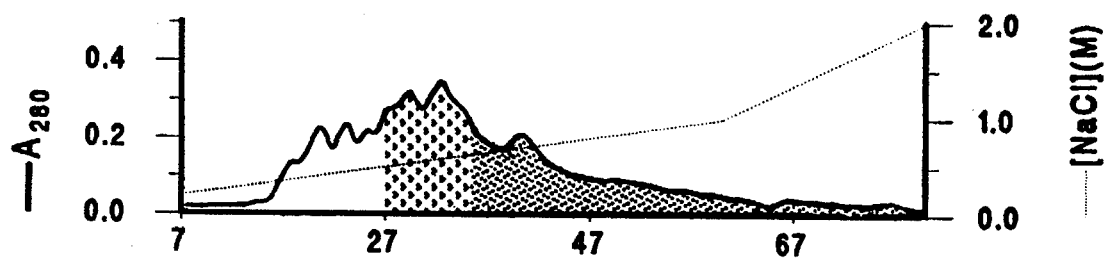
FIG. 1A is a graph of $A_{280}$ and NaCl concentration for the eluate from the phosphocellulose column in the purification of *Methanopyrus kandleri* topoisomerase V.

DNA topoisomerase V has been purified from the hyperthermophilic methanogen *Methanopyrus kandleri*. *M. kandleri* was isolated from a Guaymas Basin thermal vent submarine sediment sample taken by the research submersible Alvin (R. Huber et al., Nature 342:833–834 (1989)). It forms methane autolithotrophically using only H$_2$ and CO$_2$ as energy and carbon sources at temperatures up to 110° C., the upper temperature boundary at which living organisms have been found (K. O. Stetter, in *Frontiers of Life* (J. Tran Than Van et al., eds., Editions Frontières, Gif-sur-Yvette, 1992)).

The novel topoisomerase has properties similar to those of eukaryotic topoisomerase I, which distinguish it from all previously known prokaryotic topoisomerases. In particular, the enzyme is magnesium independent, it relaxes both negatively and positively supercoiled DNA, it makes a covalent complex with the 3' end of the broken DNA strand, it cleaves DNA at a site that is similar to the consensus sequence found for eukaryotic topoisomerases I, and it is recognized by antibody to human topoisomerase I. However, being remarkably thermostable and being able to unwind ccDNA, topoisomerase V differs from all known type 1-group B DNA topoisomerases.

I. PURIFICATION OF TOPOISOMERASE V

DNA topoisomerase V from *M. kandleri* can be purified by the following procedure: (1) lysis of the cells; (2) precipitation with polyethyleneimine and separation of the supernatant; (3) precipitation with ammonium sulfate; (4) phosphocellulose chromatography; (5) chromatography on heparin; and (6) gel filtration.

The product of this purification scheme is substantially purified *M. kandleri* DNA topoisomerase V substantially free of other enzymes acting on DNA.

A. Lysis

A suitable strain of *M. kandleri* is AV-19, DSM 24, Braunschweig, Germany. Lysis of the cells can be performed by methods generally known in the art that preserve enzymatic activity and minimize protein degradation. Preferably, lysis is carried out at about 4° C. in the presence of at least one inhibitor of proteolytic activity. Lysis is preferably carried out in a disrupting device such as a French pressure cell.

A preferable lysis buffer contains 100 mM Tris-HCl, pH 8.0 at 25° C., 0.5 M NaCl, 10 mM β-mercaptoethanol, 50 µg/ml of phenylmethylsulfonyl fluoride (PMSF), 50 µg/ml of N-tosyl-L-phenylalanine chloromethyl ketone (TPCK), 50 µg/ml of N-α-p-tosyl-L-lysine chloromethyl ketone (TLCK), 50 µg/ml of pepstatin A, 50 µg/ml of leupeptin, and 1 mM benzamidine.

Typically, a quantity of cells is thawed in a water bath at room temperature in 1 milliliter of lysis buffer per 2 grams of cells and passed through a French pressure cell at 16,000 psi to give a lysate.

B. Polyethyleneimine Precipitation

The next step is the precipitation of the lysate with polyethyleneimine (Polymin P) and the collection of the supernatant. Typically, the lysate is diluted with lysis buffer to a final volume five times the original volume of lysis buffer, and centrifuged for two hours at high speed (40,000 rpm in a Beckman Instruments (Fullerton, Calif.) Ti-50 rotor) (144,600 xg). To the recovered solution, a 5% solution of polyethyleneimine (pH 7.0) is added to the supernatant to a final polyethyleneimine concentration of 0.3%. After mixing for about 30 minutes at 0° C., the solution is centrifuged at 12,000 rpm (23,750 xg) and the supernatant saved. The supernatant includes the topoisomerase V.

C. Precipitation with Ammonium Sulfate

In the next step of purification, the supernatant from the polyethyleneimine precipitation step is precipitated with saturated ammonium sulfate. Typically, a volume of 4 M ammonium sulfate equal to about 0.9 times the volume of the polyethyleneimine supernatant is added with stirring, and then solid ammonium sulfate is added to 90% saturation. The precipitate is collected by centrifugation after decantation of the supernatant.

About half of the proteins of *M. kandleri* are in the precipitate. Substantially all of the topoisomerase V activity is found in the pellet.

Phosphocellulose Chromatography

The next step is phosphocellulose chromatography. The pellet from ammonium sulfate precipitation is redissolved in a suitable starting buffer for phosphocellulose chromatography. A preferable starting buffer is 0.2 M NaCl, 30 mM sodium phosphate, pH 7.4 at 25° C., 10 mM β-mercaptoethanol, 10% glycerol, 25 µg/ml each of PMSF, TPCK, and TLCK, 5 µg/ml of pepstatin A, 1 µg/ml of leupeptin, and 1 mM benzamidine, referred to as Buffer A+0.2 M NaCl.

The redissolved pellet is dialyzed against starting buffer and loaded onto the column. The column is washed with the starting buffer after loading. Topoisomerase V is eluded with a linear gradient running from 0.2 to 1.0 M NaCl of a buffer containing the other components of starting buffer, followed by a linear gradient from 1.0–2.0 M NaCl in the same buffer. Active topoisomerase V elutes from 0.55–0.73 M NaCl (fraction IVa) and also from 0.73–1.45 M NaCl (fraction IVb).

The resulting fractions are dialyzed against buffer B (10 mM sodium phosphate, pH 7.4 at 25° C., 10% glycerol, 2 mM β-mercaptoethanol) +0.5 M NaCl, if necessary after concentration.

E. Heparin Chromatography

The next step is heparin chromatography of the active fractions from the phosphocellulose chromatographic step. Preferably, fractions IVa and IVb are chromatographed separately on heparin. The dialyzed fractions are loaded onto a heparin column equilibrated with buffer B+0.5 M NaCl. After washing with the starting buffer the enzyme is eluted with a linear gradient of from 0.5 to 1.5 M NaCl in buffer B and fractions are collected. Active topoisomerase V elutes from about 1.0 to about 1.25 M NaCl for fraction IVa and from 0.95 to 1.25 M NaCl for fraction IVb. Preferably, the eluted topoisomerase enzyme is concentrated by rechromatography on a smaller heparin column after decrease of the sodium chloride concentration to 0.5 M by dilution with buffer B without sodium chloride. The enzyme is then re-eluted from the smaller column.

F. Gel Filtration

The final step in the purification process is gel filtration on a column capable of resolving proteins in the molecular weight range of about 50,000 daltons to about 200,000 daltons. A preferable chromatographic column comprises a HiLoad 16/60 Superdex 200 PG column (Pharmacia Biotech, Piscataway, N.J.). Typically, the concentrated topoisomerase from the heparin chromatographic step is passed through the column which has been equilibrated with 10 mM sodium phosphate, pH 7.4 at 25° C., 1 M NaCl, 5% glycerol, 2 mM β-mercaptoethanol.

Topoisomerase V from fraction IVa that has been subjected to heparin chromatography and gel filtration chromatography has a specific activity of approximately $2.0 \times 10^6$ units per milligram in an assay to determine ATP-independent and $Mg^{2+}$-independent relaxation of supercoiled pBR322 DNA. For the assay, 1 µl of topoisomerase V preparation is incubated with a 50:50 mixture of positively and negatively supercoiled pBR322 DNA (0.2 µg) and assay buffer (30 mM Tris-HCl, pH 8.0 at 25° C., 1 M potassium glutamate, and 5 mM $Na_2EDTA$) in a 10 µl reaction mixture at standard assay conditions of 88° C. for 15 minutes. The reactions were terminated by cooling them to 0° C. and adding SDS to 1%. For topoisomerase assay in crude extracts, the reactions, after termination by SDS, were treated with 400 µg/ml of proteinase K at 37° C. for one hour and then heated at 80° C. for two minutes. Topoisomerization products are analyzed by 1.5% agarose gel electrophoresis in the presence of 1.6 µg/ml chloroquine at 3 V/cm for 10 hours. One unit of activity was defined as the amount of enzyme required to relax 50% of form I pBR322 DNA (0.2 µg) under standard conditions.

SDS polyacrylamide gel electrophoresis of the peak resulting from heparin chromatography and gel filtration of phosphocellulose peak IVa indicates that only one major protein peak is present. This protein has a molecular mass of 110,000 daltons as determined by SDS polyacrylamide gel electrophoresis, although its behavior on gel filtration chromatography corresponds to that of a globular protein with a molecular weight of about 142,000 daltons. Such inconsistencies between molecular weights obtained by polyacrylamide gel electrophoresis and gel filtration are not uncommon and reflect a degree of molecular asymmetry in the protein.

The gel filtration product represents approximately a 3,620-fold purification. If this is taken to represent purity, the heparin fraction is approximately 60% pure. However, in the context of this application, the term "substantially purified" means the following: (1) at least about a 40-fold purification with respect to the cleared lysate, and (2) substantially free of other enzymes acting on DNA. Such preparations are sufficiently pure to be useable in many of the applications of DNA topoisomerase V.

The purification is summarized in Table I.

TABLE I

Purification of DNA toposiomerase V from *Methanopyrus kandleri*

| Fraction | Step | Volume ml | Total protein mg | Total activity units × $10^6$ | Specific activity units/mg | Yield % | Purification fold |
|---|---|---|---|---|---|---|---|
| I | Cleared lysate | 259 | 7020 | 3.88 | $5.5 \times 10^2$ | 100 | 1.0 |
| II | Polymin P | 265 | 7580 | 5.30 | $7.0 \times 10^2$ | 136 | 1.3 |
| III | Ammonium sulphate | 438 | 3590 | 4.38 | $1.2 \times 10^3$ | 113 | 2.2 |
| IVa | Phosphocellulose | 135 | 90.0 | 2.16 | $2.4 \times 10^4$ | 55.6 | 43.4 |
| Va | Heparin | 13 | 0.767 | 0.91 | $1.2 \times 10^6$ | 23.4 | 2150 |
| VIa | Superdex 200 | 13 | 0.390 | 0.78 | $2.0 \times 10^6$ | 20.1 | 3620 |
| IVb | Phosphocellulose | 100 | 186 | 1.50 | $8.1 \times 10^3$ | 38.6 | 14.6 |
| Vb | Heparin | 15 | 9.27 | 0.90 | $9.7 \times 10^4$ | 23.2 | 176 |
| VIb | Superdex 200 | 13 | 0.563 | 0.10 | $1.9 \times 10^5$ | 2.7 | 334 |
| VIc | Superdex 200 | 13 | 0.766 | 0.78 | $1.0 \times 10^6$ | 20.1 | 1840 |
| VId | Superdex 200 | 13 | 0.202 | 0.03 | $1.3 \times 10^5$ | 0.7 | 233 |
| IV | Phosphocellulose | 235 | 276 | 3.66 | | 94.2 | |
| V | Heparin | 28 | 10.0 | 1.81 | | 46.6 | |
| VI | Superdex 200 | 52 | 1.92 | 1.69 | | 43.5 | |

II. PROPERTIES OF TOPOISOMERASE V

A. Enzymatic Activity

The topoisomerase V of the present invention is a type 1 topoisomerase. This enzyme has both relaxing and unlinking (or unwinding) activity on ccDNA as detailed below.

1. Topoisomerase V is a Type 1 Topoisomerase

Figure 11:
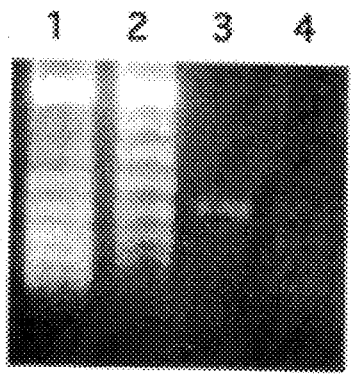
FIG. 11 is a photograph of an agarose gel showing the relaxation of a unique topoisomer by M. kandleri topoisomerase V, with native pUC19 DNA or its unique topoisomer as substrate, and with electrophoresis in the presence of 2 µg/ml of chloroquine.

Topoisomerase V from *M. kandleri* is a type 1 topoisomerase because it changes the linking number of a unique pUG19 DNA topoisomer in steps of one (FIG. 11).

The Activity of DNA Topoisomerase V is Not Affected by Single-Stranded DNA

The activity of DNA topoisomerase V is not affected by the presence of single-stranded DNA. FIG. 12 shows that the addition of single-stranded DNA φX174 DNA does not affect the relaxation of negatively or positively supercoiled pBR322 plasmid DNA by topoisomerase V at 70° C. and 90° C. at any φX174:pBR322 ratio up to 4.9:1. Lack of inhibition by single-stranded DNA distinguishes this enzyme from other thermophilic type 1 topoisomerases, topoisomerase I (reverse gyrase) and D. amylolyticus topoisomerase III which belong to group A and from mesophilic group B topoisomerases (J. J. Champoux in *DNA Topology and Its Biological Effects* (N. R. Cozzarelli and J. C. Wang, eds., Cold Spring Harbor Laboratory Press, New York, 1990), pp. 217–242)

From the inability of single-stranded DNA to inhibit topoisomerase V and from the ability of topoisomerase V to relax positively supercoiled DNA, Applicant believes that topoisomerase V requires double-stranded regions of DNA for binding and topoisomerization, although Applicant does not intend to be bound by this theory and it is not required to account for the properties of the enzyme.

3. Ionic Conditions for Relaxation and Unlinking

The relaxing activity of topoisomerase V (occurs below the melting range of linear DNA) on supercoiled DNA in different ionic conditions of 80° C., 88° C., and 95° C. is shown in FIGS. 9A–9D and 10A–10D and summarized in Table II. In FIGS. 9A–9D, a mixture of positively and negatively supercoiled DNA was used as the substrate and the results were analyzed by gel electrophoresis in the presence of chloroquine to separate positively from negatively supercoiled substrates. In FIGS. 10A–10D, a negatively supercoiled substrate was used and the products were analyzed by gel electrophoresis without chloroquine. In both FIGS. 9A–9D and FIG. 10A–10D, the quantity of the enzyme was low enough to prevent complete relaxation and to monitor relative enzymatic activity by the extent of the conversion of the substrate to the product.

Complete relaxation of positively supercoiled DNA and practically complete relaxation of negatively supercoiled DNA by topoisomerase V is observed at 1.55 M potassium glutamate, 88° C., the condition considered optimal for DNA relaxation. Examples of the enzymatic activity include partial relaxation of supercoiled DNA, complete relaxation of a fraction of supercoiled DNA substrates, and complete relaxation of positively supercoiled DNA while having little activity on negatively supercoiled DNA. The enzyme can act distributively (i.e., the enzyme dissociates from the DNA after each catalytic cycle) or processively (i.e., the enzyme requires several catalytic cycles to occur before the enzyme dissociates). The enzyme also prefers positively supercoiled over negatively supercoiled DNA, although it acts on both.

The substitution of chloride anion for glutamate anion substantially decreases the optimal salt concentration for relaxation from about 1.5 M to 0.5 M. The use of sodium cation instead of potassium decreases the optimum further by about 0.15 M so the optimum concentration of sodium chloride is about 0.30 to 0.35 M. The specific activity of the enzyme at optimal salt concentration is virtually salt-independent. There is virtually no effect of magnesium on relaxation by the enzyme, and EDTA does not inhibit the reaction. At 88° C., activity was detected at potassium glutamate concentrations of up to 3.1 M.

The ionic effects on the unlinking activity of topoisomerase V (the unlinking activity reveals itself in the melting range of linear DNA) differ from those on its relaxing activity. The data are shown in FIGS. 13A–13D. The unwinding of the topoisomers by topoisomerase V is more sensitive to high NaCl concentration: no unlinking occur at NaCl concentration as high as 0.5 M at 95° C., while the relaxing activity is still observed up to 0.65 M at 88° C. At 0.25–2.1 M potassium glutamate topoisomerase V uses the substrate DNA at 95° C. for unlinking more efficiently than at 80° or 88° C. for relaxation, if the extent of the conversion to the product is compared.

The data on the extent of the conversion to the product in the presence of $MgCl_2$ show that magnesium does not affect neither relaxation nor unlinking activities of topoisomerase V above 90 mM of monovalent salt. On the other hand, there is no effect of NaCl below 90 mM on the DNA unlinking at 95° C. or DNA "re-relaxation" at 80° C. in the presence of 5 mM $MgCl_2$. Applicant believes that it is likely due to the stabilizing effect of magnesium on the DNA duplex, although Applicant does not intend to be bound by this theory.

TABLE II

Effect of different ions on the DNA relaxation activity by Mka topoisomerase V

|  | Concentration (M) at which the activity is maximal | | | Highest concentration (M) at which the activity was detected | | |
| --- | --- | --- | --- | --- | --- | --- |
|  | K-Glu | KCl | NaCl | K-Glu | KCl | NaCl |
| 80° C., EDTA | 1.5 | 0.45 | 0.30 | 2.1 | 0.55 | 0.45 |
| 80° C., $MgCl_2$ | 1.5 | 0.45 | 0.30 | 2.1 | 0.45 | 0.45 |
| 88° C., EDTA | 1.5 | 0.50 | 0.35 | 3.1 | 0.65 | 0.65 |

4. Reversibility of Topoisomerase V Binding to DNA

Figure 14A:
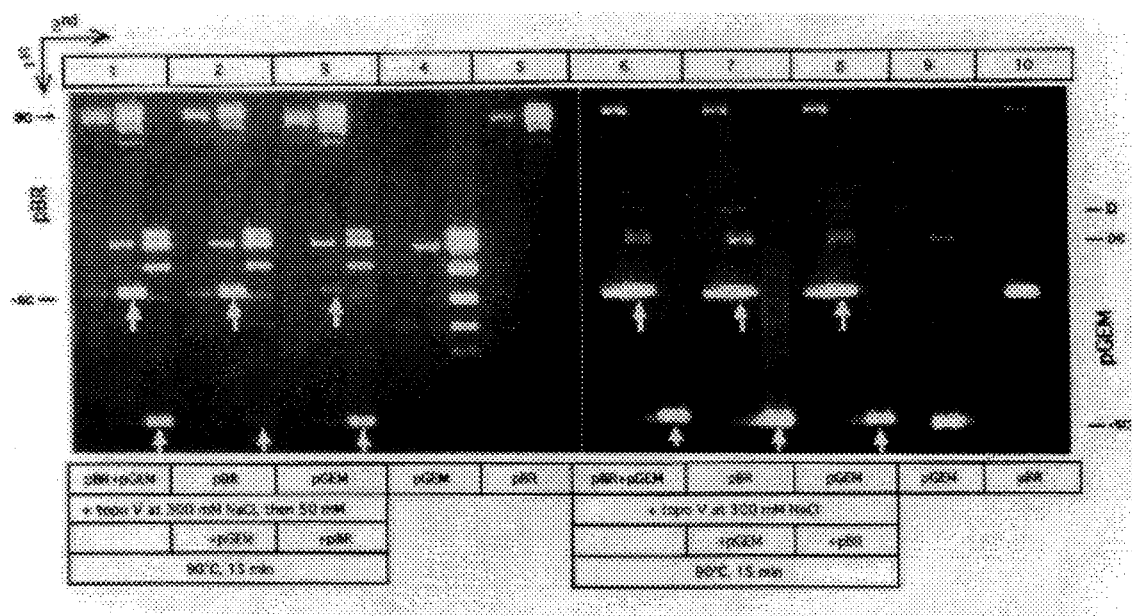
FIG. 14A is a photograph of an two-dimensional agarose gel showing competition of *M. kandleri* topoisomerase V for substrate DNA with relaxed pBR322 DNA and relaxed pGEM3 DNA at low or high sodium chloride concentration, the electrophoresis being done without chloroquine in the first dimension and with 4 µg/ml chloroquine in the second dimension.
Figure 14B:
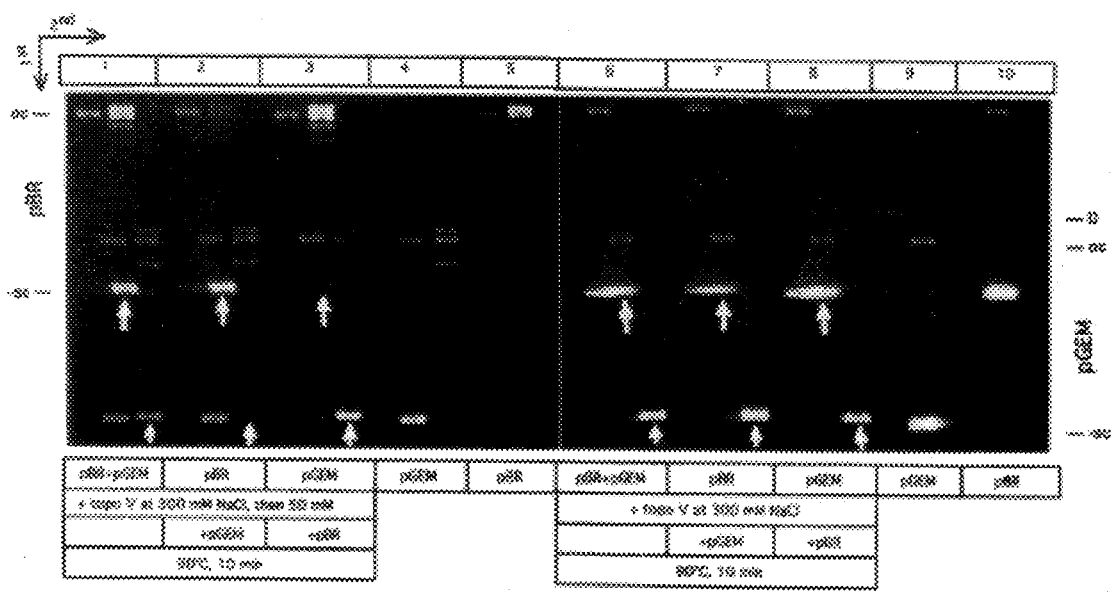
FIG. 14B is a photograph of an two-dimensional agarose gel showing competition of *M. kandleri* topoisomerase V for substrate DNA with relaxed pBR322 DNA and composite preparation contained supercoiled and relaxed pGEM3 DNA at low or high sodium chloride concentration, the electrophoresis being done without chloroquine in the first dimension and with 4 µg/ml chloroquine in the second dimension.

At 300 mM NaCl, topoisomerase V freely dissociates and binds DNA (FIGS. 14A and 14B). This is shown by experiments in which the topoisomerase was prebound to one type of DNA and then a competitor DNA was added. The results of these experiments indicate that the topoisomerase V can dissociate from the type of DNA to which it was prebound and bind to another type of DNA. At lower ionic strength, the enzyme remains bound to the original substrate DNA, unlinking it, but does not bind significantly to competitor DNA. Remarkably, topoisomerase V unlinks DNA duplex at 50 mM NaCl in a highly processive mode without magnesium, by contrast to eukaryotic topoisomerase I which always requires magnesium for processivity (P. A. Der Garabedian et al., *Biochemistry* 30:9940–9947 (1990)).

5. Inhibitors of Topoisomerase V

Figure 15:
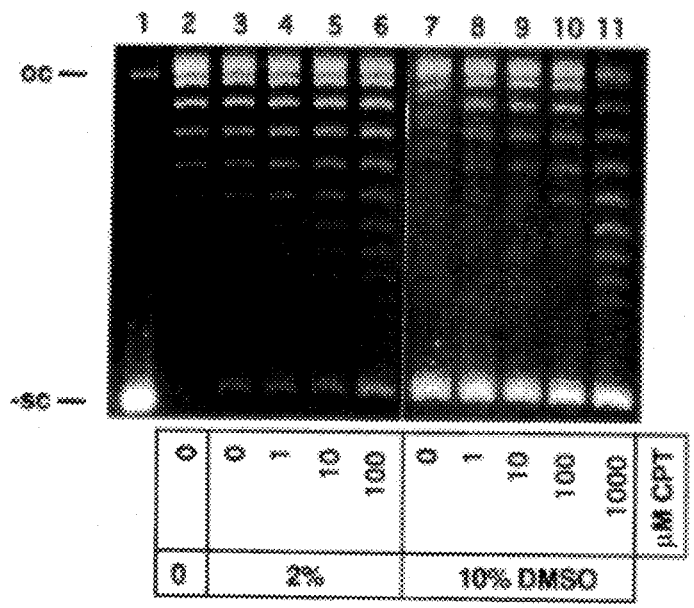
FIG. 15 is a photograph of an agarose gel showing the effect of dimethyl sulfoxide and camptothecin on the activity of *M. kandleri* topoisomerase V with pBR322 DNA as substrate at 70° C. in 30 mM Tris-HCl, pH 8.0 (at 25° C.), 1 M potassium glutamate, and 5 mM Na$_2$EDTA.

Camptothecin, which is a specific inhibitor of eukaryotic topoisomerase I from different species, has limited effect against the topoisomerase V of the present invention. However, dimethyl sulfoxide, which is used as a solvent for camptothecin and does not inhibit eukaryotic topoisomerases by itself, inhibits topoisomerase V (FIG. 15). This distinguishes the enzyme from eukaryotic topoisomerase I.

B. Formation of Covalent Complex with DNA at 3'-End

*M. kandleri* topoisomerase V covalently binds to the 3'-end of the DNA strand that it cleaves during the unlinking or unwinding reaction. Shorter DNA fragments appeared on a denaturing gel if 3'-labeled DNA was incubated with topoisomerase V followed by the addition of protein denaturant (FIG. 17), but not if the DNA was labeled at the 5'-end. Thus, the enzyme covalently binds to the 3'-end of the broken DNA strand, preventing the 5'-labeled cleavable complex from entering the gel. The major topoisomerase V cleavage site (FIG. 18) on a 280-bp fragment of pGEM1 DNA has a sequence similar, but not identical, to the sequence of the consensus cleavage site for eukaryotic topoisomerase I (B. J. Bonven et al., *Cell* 41:541–551 (1985)).

Figure 19:
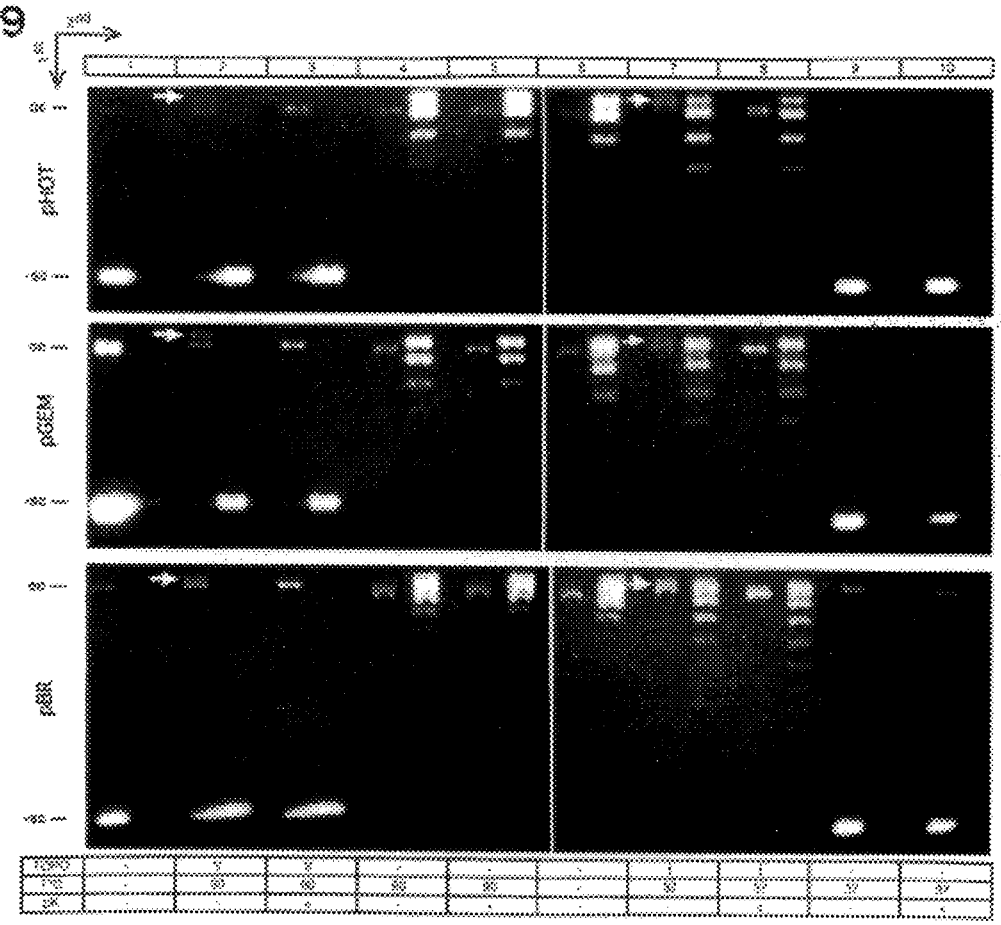
FIG. 19 is a photograph of a two-dimensional agarose gel showing covalent complex formation between relaxed or supercoiled plasmid DNAs and *M. kandleri* topoisomerase V, the electrophoresis being done in the presence of 0.1% SDS.

If *M. kandleri* topoisomerase V is incubated with relaxed closed circular DNA, such as pBR322, pGEM3, or a derivative of pUC12 containing the consensus cleavage site for eukaryotic topoisomerase I and designated pHOT1, a covalent complex containing the topoisomerase and open circular DNA can be isolated (Example 12; FIG. 19)). The topoisomerase in this complex is covalently bound to the broken strand, as the complex is treated with protein denaturants such as sodium dodecyl sulfate.

Accordingly, the present invention also includes a complex comprising the topoisomerase of the present invention non-covalently bound to DNA, as well as a complex comprising the topoisomerase of the present invention covalently linked to the 3'-end of a DNA strand, which can be the 3'-end of a broken strand of open circular DNA.

Antibody Reactivity

Figure 6:
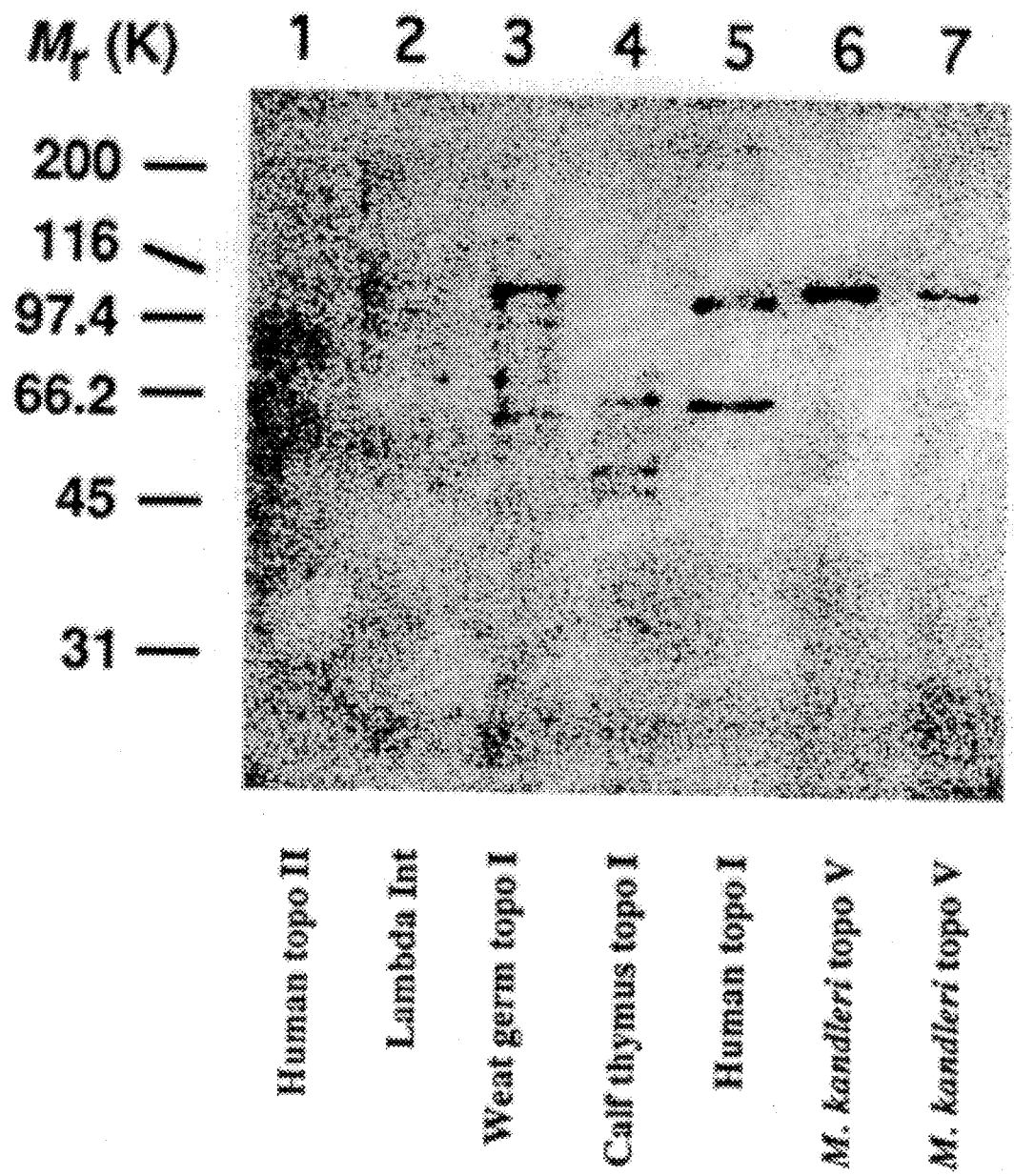
FIG. 6 is an immunoblot of human topoisomerase II, λ Int protein, wheat germ topoisomerase I, calf thymus topoisomerase I, human topoisomerase I, and M. kandleri topoisomerase V with antibody to human topoisomerase I.

*M. kandleri* topoisomerase V reacts with antibody raised against human topoisomerase I (FIGS. 6–7). Human topoisomerase II and λ Int protein, which relaxes negatively and positively supercoiled DNA and binds covalently to the 3'-end of the broken DNA strand, do not react with antibody to human topoisomerase I.

The described properties of *M. kandleri* topoisomerase V enzyme identify it as a type 1-group B DNA topoisomerase (Table III). This is the first prokaryotic enzyme in this group.

Thus, a method of detecting and/or determining the *M. kandleri* topoisomerase V of the present invention can comprise the steps of:

(1) reacting the topoisomerase of the present invention with anti-human topoisomerase I antibody; and (2) detecting and/or determining the topoisomerase V by detecting and/or determining an antigen-antibody complex between the topoisomerase and the antibody.

TABLE III

Classification of type I DNA topoisomerases

| TYPE I DNA TOPISOMERASES | GROUP A | | | GROUP B | |
| --- | --- | --- | --- | --- | --- |
| Location | bacteria, chloroplasts, yeast | | | eukaryotic nuclei, mitochondria, poxviruses, *Methanopyrus kandleri* | |
| Covalent complex with the broken DNA strand | 5'-P | | | 3'-P | |
| Substrate DNA for cleavage/religation | single-stranded | | | double-stranded | |
| Activity on positively supercoiled duplex DNA | − | | | + | |
| Mg²⁺ requirement for topoisomerization | + | | | − | |
| Strong cleavage sites | CNNN↑ | | other | (C/T)CCTT↑ | hexadecamer |
| ATP requirement for catalytic activity | + | − | − | − | − |
| ΔLk per one cycle | +1 (pos. supercoiling) | ±1 (relaxation) | ±1 (relaxation) | ±1 (relaxation) | ±1 (relaxation) |
| Specific drugs | − | − | − | − | camptothecin |
| Examples | Dam, Mka, Sac topo I (rev. gyrase) | Eco, Mlu topo I | Dam, Eco, Sce topo III | VVir topo | Mka topo V | Hsa, Sce, Tth topo I |

The consensus for DNA cleavage by Eco and Dam topoisomerases III has not been established and was shown to be different from CNNN↑, Sce topoisomerase III has a strong preference for ANN↑. Hexadecameric consensus for DNA cleavage by eukariotic topoisomerases I: AGACTT↑AGA(A/G)AAA(A/T)(A/T)(A/T) was derived from the Tetrahymena rDNA repeats. Dam - *Desulfurococcus amylalyticus*, Eco - *Escherichia coli*, Hsa - *Homo sapiens*, Mka - *Methanopyrus kandleri*, Mlu - *Micrococcus luteus*, Sac - *Sulfolobus acidocaldarius*, Sce - *Saccharomyces cerevisiae*, Tth - *Tetrahymena thermophila*, VVir - Vaccinia virus Partial Amino Acid Sequences The amino-terminal amino acid sequence of *M. kandleri* DNA topoisomerase V is Ala-Leu-Val-Tyr-Asp-Ala-Glu-Phe-Val-Gly-Ser-Glu-Arg-Glu-Phe-Glu-Glu-Glu-Arg-Glu-Thr-Phe-Leu-Lys-Gly-Val-Lys-Ala-Tyr-Asp-Gly-Val-Leu-Ala-Thr-Arg-Tyr-Arg-Tyr-Leu-Met-Glu-Arg-Ser-Ser-Ser-Ala (SEQ ID NO: 3).

Several proteolytic fragments of topoisomerase V have been generated with the proteolytic enzyme endoproteinase Lys-C (Promega, Madison, Wis.), which cleaves at the carboxylic side of lysine (K). Five such fragments have been generated: Fragment I, of about 50,000 daltons; Fragment II, a fragment of about 42,000 daltons; Fragment III, a fragment of about 36,000 daltons; Fragment IV, a fragment of about 33,000 daltons; and Fragment V, a fragment of about 25,000 daltons. Fragment III is from the carboxyl-terminus of the protein. In addition, fragments of about 75,000 daltons and 55,000 daltons (Fragment N1 and N2, respectively) can be isolated and, by its protein sequence, are from the amino-terminus of the enzyme (Example 13). Although Applicant does not intend to be bound by this theory, at least Fragment III and Fragment N1 are believed to represent stable domains within the enzyme and can be used as immunogens for the production of antibodies, including monoclonal antibody if desired. Such antibody is an aspect of the present invention.

The partial amino acid sequence of Fragment IV is Lys-Ser-Gly-Arg-Gln-Glu-Arg-Ser-Glu-Glu-Glu-Trp-Lys- Glu-Trp-Leu-Glu-Arg-Lys-Val-Gly-Glu-Gly-Arg-Ala-Arg-Arg-Leu-Ile-Glu-Tyr-Phe-Gly-Ser-Ala (SEQ ID NO: 1).

The partial amino acid sequence of Fragment V is Lys-Tyr-Gly-Ser-Ala-Ser-Ala-Val-Arg-Arg-Leu-Pro-Val-Glu-Glu-Leu-Arg-Glu-Leu-Gly-Phe-Ser-Asp-Asp-Glu (SEQ ID NO: 2).

The availability of the amino-terminal amino acid sequence of *M. kandleri* topoisomerase V means that the present invention includes thermostable type 1-group B DNA topoisomerases possessing the amino-terminal amino acid sequence of *M. kandleri* topoisomerase V. In this context, the term "thermostable" is defined as possessing detectable relaxing activity at a temperature of 50° C. or higher. Additionally, enzymes containing conservative amino acid substitutions within this sequence are also within the scope of the invention. Such conservative amino acid substitutions include, but are not limited to, substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine (A) and valine (V). Methionine (M), which is relatively hydrophobic, can frequently be interchanged with leucine (L) and isoleucine (I), and sometimes with valine (V). Lysine (K) and arginine (R) are frequently interchangeable in locations in which the significant feature of the amino acid residue is its charge and the differing pK's of these two amino acid residues are not significant. Still other changes can be considered "conservative" in particular environments.

The present invention also includes thermostable type 1-group B DNA topoisomerases possessing at least one of the following amino acid sequences that is from Fragment IV or Fragment V and is unequivocally known:

(1) Lys-Ser-Gly-Arg-Gln-Glu-Arg-Ser-Glu-Glu-Glu-Trp-Lys-Glu-Trp-Leu-Glu-Arg-Lys-Val-Gly-Glu-Gly-Arg-Ala-Arg-Arg-Leu-Ile-Glu-Tyr-Phe-Gly-Ser-Ala (SEQ ID NO: 1) (from Fragment IV); and (2) Lys-Tyr-Gly-Ser-Ala-Ser-Ala-Val-Arg-Arg-Leu-Pro-Val-Glu-Glu-Leu-Arg-Glu-Leu-Gly-Phe-Ser-Asp-Asp-Glu (SEQ ID NO: 2) (from Fragment V).

The invention further includes thermostable type 1-group B DNA topoisomerases possessing at least one amino acid sequence related to sequence (1) or (2) by one or more conservative amino acid substitutions.

Also within the scope of the present invention are modifications of these enzymes, including, but not limited to, enzymes bound to solid supports.

III. USE OF TOPOISOMERASE ACCORDING TO THE PRESENT INVENTION

Topoisomerase V according to the present invention can be used, as described above, either to relax supercoiled DNA or to unlink ccDNA.

In general, the unlinking reaction comprises treating a ccDNA with the enzyme of the present invention at a temperature at least as high as the melting range of the linear form of treated DNA and ionic conditions that allow the enzyme to bind to DNA and catalyze the unlinking reaction; the enzyme binds to DNA and catalyzes the unlinking reaction, driven by DNA melting, and ccDNA with Lk lower than the Lk of the DNA before treatment is produced.

This reaction is equally applicable to any procedure that involves primer annealing and/or elongation, i.e., PCR, LCR, hybridization probe preparation, including DNA template preparation for hybridization of large probes.

The relaxation reaction comprises treating a supercoiled DNA with the enzyme of the present invention at a temperature below the melting range of linear form of the treated ccDNA and ionic conditions that allow the enzyme to bind to DNA and catalyze the relaxation reaction to produce at least partially relaxed DNA. The DNA to be relaxed can be positively supercoiled DNA, negatively supercoiled DNA, or a mixture of the two types of supercoiled DNA.

These relaxation and unlinking reactions are particularly useful for manipulation of DNA conformation, for preparation of ccDNA with desired degree of supercoiling using only one enzyme and varying only ionic conditions and temperature.

A unique salt tolerance of the enzyme makes it an indispensable tool in chromatin reconstitution in vitro.

Topoisomerase V can be used to form a covalent complex with DNA. The method of covalent complex formation comprises:

(1) incubating the topoisomerase of the present invention with DNA under ionic conditions allowing the binding of the topoisomerase to the DNA and the breaking of one strand by the topoisomerase; and (2) denaturing of the topoisomerase leaving a covalent complex between the topoisomerase and the DNA.

Topoisomerase V can also be used as a specific endonuclease. The method of use of topoisomerase V as a specific endonuclease comprises:

(1) incubating the topoisomerase of the present invention with DNA under ionic conditions allowing the binding of the topoisomerase to the DNA and the breaking of one strand by the topoisomerase at a specific sequence; and (2) then denaturing the topoisomerase yielding cleaved DNA.

Figures 5A, 18:
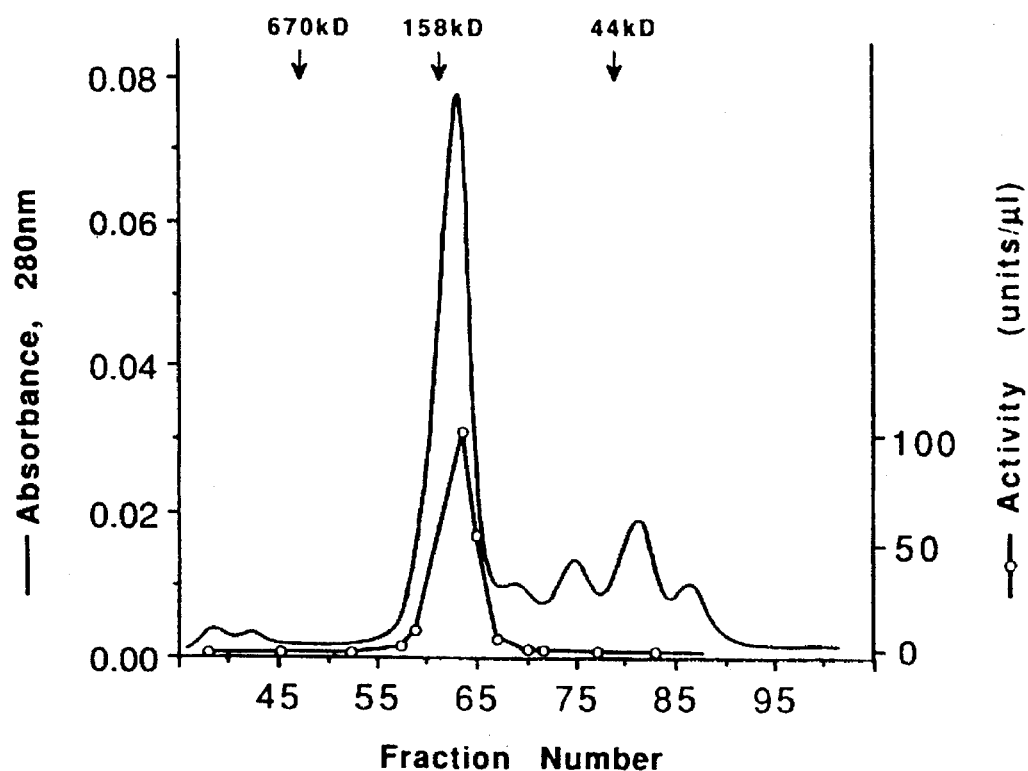
FIG. 5A is a graph of the $A_{280}$ (- - -) and topoisomerase V activity (- - -o- - -) of the eluate from gel filtration of fraction Va.
FIG. 18 shows the cleavage site of *M. kandleri* topoisomerase V on pGEM1 DNA in comparison to the consensus eukaryotic topoisomerase I site.

The sequence at which cleavage occurs, as shown in FIG. 18, is related to the site of cleavage by eukaryotic topoisomerase I enzymes.

Additionally, topoisomerase V can be used to produce an activated DNA substrate with at least a single amino acid residue covalently bound to the 3'-$PO_4$ terminus of a DNA strand adjacent to the recognition site of the topoisomerase of the present invention. The process comprises:

(1) incubating the topoisomerase with DNA under ionic conditions allowing the binding of the topoisomerase to DNA and the breaking of one strand by the topoisomerase at a specific sequence; and (2) then denaturing the topoisomerase and hydrolyzing the topoisomerase with a nonspecific protease.

The purified protein can also be used to prepare antibodies, both polyclonal antibodies and monoclonal antibodies. A protein of molecular weight about 110,000 is sufficiently large that it does not need to be coupled to a carrier such as keyhole limpet hemocyanin to be immunogenic. Methods for the preparation of polyclonal antibodies are well-known in the art and need not be described in detail. Such methods are disclosed, for example, in E. Harlow & D. Lane, *Antibodies: A Laboratory Manual* (Cold Spring Harbor Laboratory, Cold Spring Harbor, N.Y., 1988), pp. 53–137, incorporated herein by this reference.

Once polyclonal antibodies are produced, antibody-producing cells can be fused with appropriate melanoma cells to form hybridomas in order to produce monoclonal antibodies. Such monoclonal antibodies can be produced by techniques well-known in the art; typically, developments and adaptations of the basic technique of G. Köhler & C. Milstein, "Continuous Cultures of Fused Cells Secreting Antibody of Predefined Specificity", Nature 256:495–497 (1975), incorporated herein by this reference, are used. Such developments and adaptations are described, for example, in Harlow & Lane, Antibodies: A Laboratory Manual, supra, pp. 139–281, incorporated herein by this reference.

EXAMPLES

The invention is illustrated by the following Examples. These examples are for exemplification purposes only and do not limit the invention.

Example 1

Purification of DNA Topoisomerase V from *Methanopyrus kandleri*

Materials and Methods

*Methanopyrus kandleri* strain AV-19, DSM 6324, deposited on Jan. 30, 1991 with the Deutsche Sammlung von Mikroorganismen und Zellkulturen (DSM), Mescheroder Weg 10, Brauschsweig, Germany D-58124, and available without restrictions from that depository, was used. The cells were grown in BSM medium at 100° C. in a 300-liter enamel protected fermentor (HTE Bioengineering, Wald, Switzerland) with stirring and continuous gassing ($H_2/CO_2$, 80:20). Exponentially growing cells were rapidly cooled and harvested with a separator (Westfalia, Germany). The cells were stored at −70° C.

Protease inhibitors phenylmethylsulfonyl fluoride (PMSF), N-tosyl-L-phenylalanine chloromethyl ketone (TPCK), N-α-p-tosyl-L-lysine chloromethyl ketone (TLCK), pepstatin A, leupeptin, and benzamidine were from Calbiochem (La Jolla, Calif.). β-mercaptoethanol was from Fisher (Pittsburgh, Pa.), polyethyleneimine (Polymin P) was from Sigma (St. Louis, Mo.), ammonium sulfate was from BRL (Gaithersburg, Md.), and glycerol was from Mallinckrodt (Chesterfield, Mo.). Phosphocellulose P11 was from Whatman (Clifton, N.J.). HiTrap Heparin columns (1 ml and 5 ml volume), and HiLoad 16/60 Superdex 200 PG gel filtration columns were from Pharmacia LKB (Piscataway, N.J.). Centriprep 30 concentration cartridges were from Amicon (Beverly, Mass.).

Methods of Protein Characterization

Protein concentrations were determined spectrophotometrically. Protein compositions of the fraction were analyzed by sodium dodecyl sulfate-polyacrylamide gel electrophoresis on Bio-Rad (Richmond, Calif.) Mini-Protein II according to the method of Laemmli or using Bio-Rad precast gels. The gels were stained with silver using the Bio-Rad silver stain kit or with Coomassie G-250 brilliant blue according to the method of Merril (C. R. Merril in *Protein Purification* (M. P. Deutscher, ed., Academic Press, San Diego, 1990), pp. 685–687)).

Topoisomerase Assay

Topoisomerase V activity was assayed by ATP-independent and $Mg^{2+}$-independent relaxation of supercoiled pBR 322 DNA. An aliquot (1 μl) of topoisomerase V preparation was incubated with a 0.2 μg of a 50:50 mixture of positively and negatively supercoiled pBR322 DNA in "standard" buffer (30 mM Tris-HCl, pH 8.0 at 25° C., 1 M potassium glutamate, and 5 mM $Na_2EDTA$) in a 10- μl reaction mixture at "standard" conditions of 88° C. for 15 minutes. The reactions were terminated by rapidly cooling to 0° C. and adding sodium dodecyl sulfate to 1% concentration. For topoisomerase assay in crude extracts, the reactions, terminated by SDS, were treated with proteinase K (400 μg/ml at 37° C. for one hour) and then heated at 80° C. for two minutes. The topoisomerization products were analyzed by 1.5% agarose gel electrophoresis in the presence of 1.6 μg/ml chloroquine at 3 V/cm for ten hours. One unit of activity was defined as the amount of enzyme required to relax 50% of form I pBR322 DNA (0.2 μg) in standard buffer in 15 minutes at 88° C.

Protein Purification

All steps were performed at 4° C. unless indicated. Chromatography was done on a LKB liquid chromatography system composed of a HPLC pump, a variable wavelength monitor reading at 280 nm, a controller, a 2-channel recorder, and a rack.

*M. kandleri* cells (120 g wet weight) were thawed in a water bath at room temperature in 60 ml lysis buffer (100 mM Tris-HCl, pH 8.0 at 25° C., 0.5 M NaCl, 10 mM β-mercaptoethanol, 50 μg/ml each of PMSF, TPCK, TLCK, pepstatin A, and leupeptin, and 1 mM benzamidine) and passed through a French pressure cell (American Instrument (Baltimore, Md.) at 16,000 psi. The recovered solution was diluted with lysis buffer to a final volume of 300 ml and centrifuged for two hours at 40,000 rpm in a Beckman Instruments (Fullerton, Calif.) Ti-50 rotor (fraction I, 259 ml). A 5% solution of polyethyleneimine (Polymin P) (pH 7.0) was added dropwise to the supernatant with constant stirring to a final concentration of 0.3%. After mixing for 30 minutes at 0° C., the solution was centrifuged at 2,000 rpm for 40 minutes in a Sorvall RC-5B centrifuge. The supernatant was saved (fraction II, 265 ml) and 245 ml of 4 M ammonium sulfate was added under stirring. Then ammonium sulfate was added to 90% saturation and the solution was left in a cold room overnight with stirring. Not all of the ammonium sulfate dissolved. The supernatant (545 ml) was decanted and centrifuged at 11,000 rpm in a Sorvall RC-5B centrifuge for two hours.

The pellet from the ammonium sulfate precipitation was dissolved in 400 ml starting buffer for phosphocellulose chromatography (Buffer A+0.2 M NaCl). Buffer A is 30 mM sodium phosphate, pH 7.4 at 25° C., 10 mM β-mercaptoethanol, 10% glycerol, 25 μm each of PMSF, TPCK, and TLCK, 5 μg/ml pepstatin A, 1 μg/ml leupeptin, and 1 mM benzamidine. The dissolved pellet was dialyzed against two liters of the same buffer with two changes (fraction III, 438 ml). After centrifugation, the solution was loaded onto a phosphocellulose P11 column (Whatman) (2.6×30 cm) equilibrated with buffer A+0.2 M NaCl. After loading, the column was washed with three volumes of buffer A+0.2 M NaCl. Topoisomerase V was eluted with a 600-minute linear gradient of 0.2 to 1.0 M NaCl in Buffer A at 1.5 ml/min, followed by a 400-minute linear gradient of 1.0 to 2.0 M NaCl in Buffer A. Fractions of 15 ml were collected and assayed for DNA relaxation activity. Active fractions were combined into two pools: A first pool of 0.55–0.73 M NaCl (135 ml) and a second pool of 0.73–1.45 M NaCl (620 ml). The latter was concentrated in Centriprep 30 cartridges to a final volume of 100 ml.

Figure 1B:
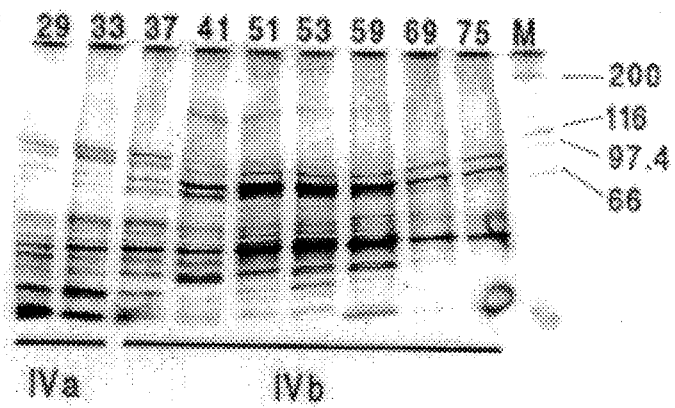
FIG. 1B is a photograph of a silver-stained 4–15% gradient polyacrylamide gel showing the protein compositions of fractions in the eluate and indicating the fractions taken as Fractions IVa and IVb.

FIG. 1 shows the results of phosphocellulose chromatography. The $A_{280}$ and NaCl concentration for the eluate from the phosphocellulose column are shown (FIG. 1A), together with a photograph of a silver-stained 4–15% SDS-polyacrylamide gel showing the protein compositions of fractions in the eluate and indicating the fractions taken for further purification as Fractions IVa and IVb (FIG. 1B). For the polyacrylamide gel, 5 µl (fractions 29–41) or 20 µl (fractions 51–75) were electrophoresed.

Both pools were dialyzed against Buffer B plus 0.5 M NaCl. Buffer B was 10 mM sodium phosphate, pH 7.4 at 25° C., 10% glycerol, 2 mM β-mercaptoethanol (Fraction IVa, 135 ml, and fraction IVb, 100 ml respectively.)

Fraction IVa was loaded onto a 5-ml HiTrap heparin column, equilibrated with buffer B plus 0.5 M NaCl. After the column was washed with 5 volumes of buffer B plus 0.5 M NaCl, a 100-minute linear gradient of 0.5–1.5 M NaCl in buffer B at 0.5 ml/min was applied.

Figure 2A:
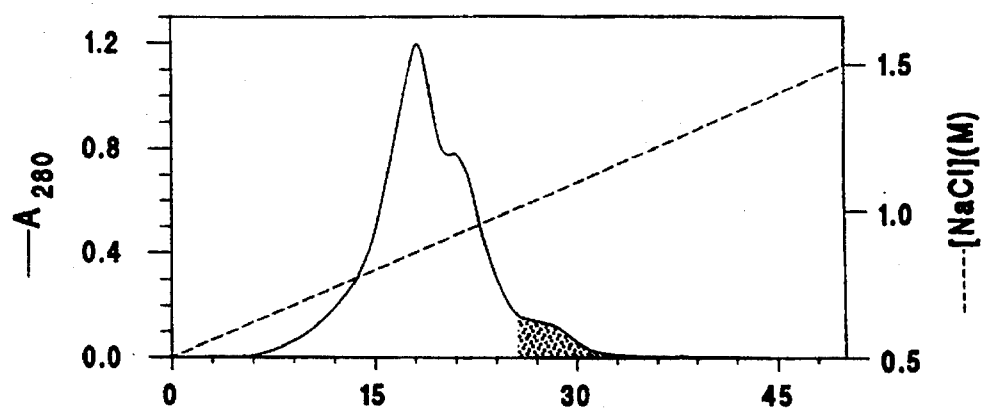
FIG. 2A is a graph of $A_{280}$ and NaCl concentration for the eluate from the heparin chromatography of Fraction.
Figure 2B:
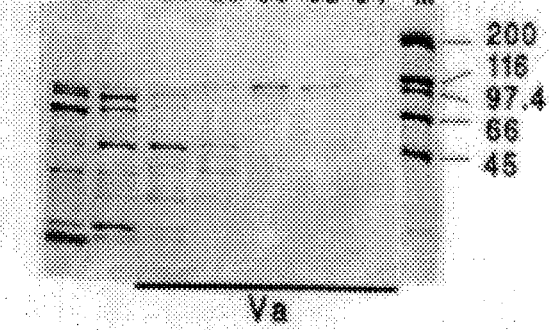
FIG. 2B is a photograph of a Coomassie blue-stained 4–15% gradient polyacrylamide gel showing the protein compositions of fractions in the eluate and indicating the fractions taken as Fraction Va.

FIG. 2 shows the results of heparin chromatography of Fraction IVa. The $A_{280}$ and NaCl concentration are shown (FIG. 2A), along with a photograph of a Coomassie blue-stained 4–15% gradient SDS-polyacrylamide gel showing the protein compositions of fractions in the eluate and indicating the fractions taken as Fraction Va (FIG. 2B). For the polyacrylamide gel, 5-µl aliquots of the fractions were electrophoresed. Topoisomerase was a major protein band in fractions 30 and 32.

Active fractions (1 ml) between 1.0–1.25 M NaCl were pooled (fraction Va, 13 ml), and concentrated on a 1-ml HiTrap heparin column by decreasing the sodium chloride concentration to 0.5 M by dilution with buffer B without sodium chloride, loading the sample on the smaller column and re-eluting with the linear gradient of NaCl. The concentrate was passed through a HiLoad 16/60 Superdex 200 PG column equilibrated with 10 ml sodium phosphate, pH 7.4 at 25° C., 1 M NaCl, 5% glycerol, 2 mM β-mercaptoethanol (fraction Va, 13 ml).

Figure 3A:
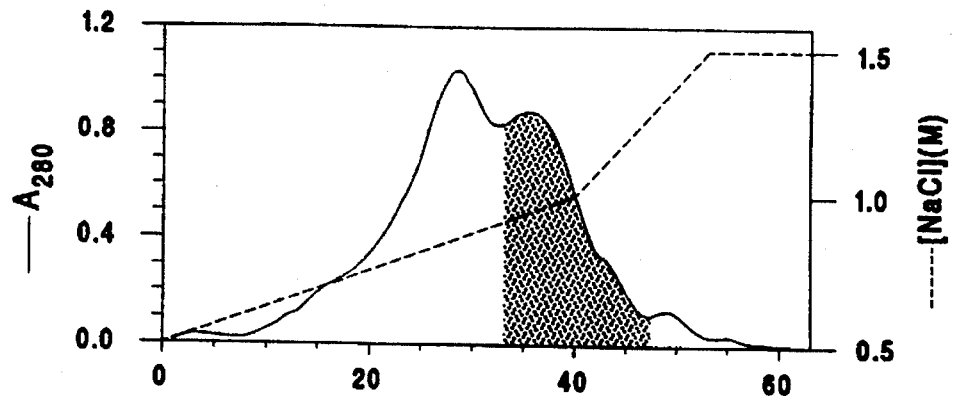
FIG. 3A is a graph of $A_{280}$ and NaCl concentration for the eluate from the heparin chromatography of Fraction IVb.
Figure 3B:
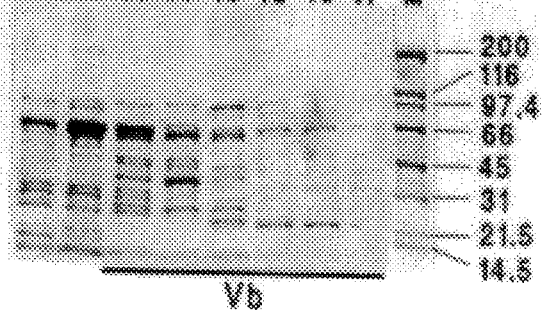
FIG. 3B is a photograph of a Coomassie blue-stained 4–15% gradient polyacrylamide gel showing the protein compositions of fractions in the eluate and indicating the fractions taken as Fraction Vb.
Figure 4A:
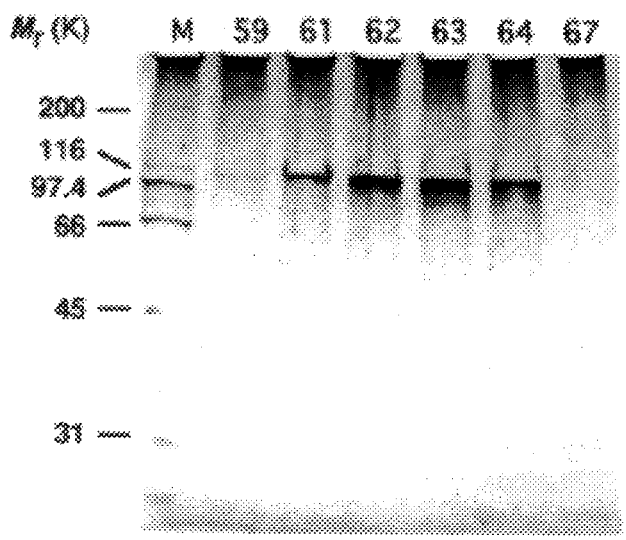
FIGS. 4A, 4B, 4C and 4D are a photograph of silver-stained 7.5% polyacrylamide gels showing the protein compositions of fractions from the eluate resulting from gel filtration of Fractions Va, Vb, Vc, and Vd from the purification of M. kandleri topoisomerase.
Figure 4B:
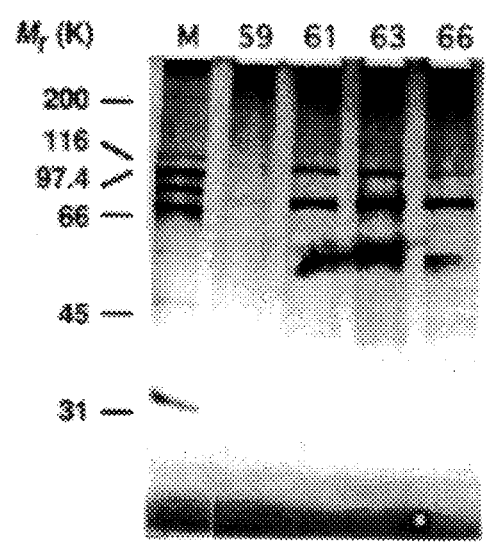
Figure 4C:
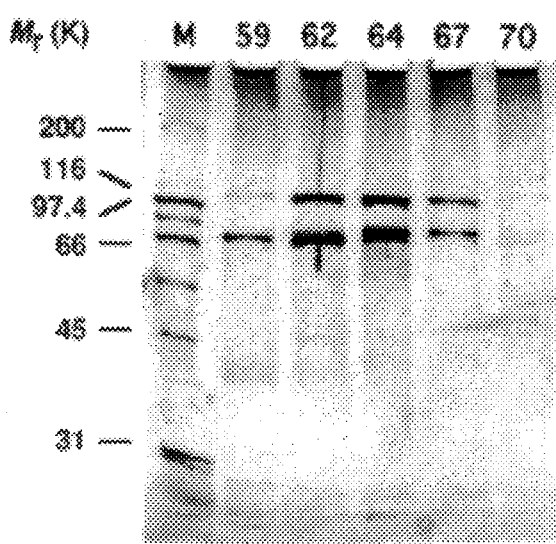
Figure 4D:
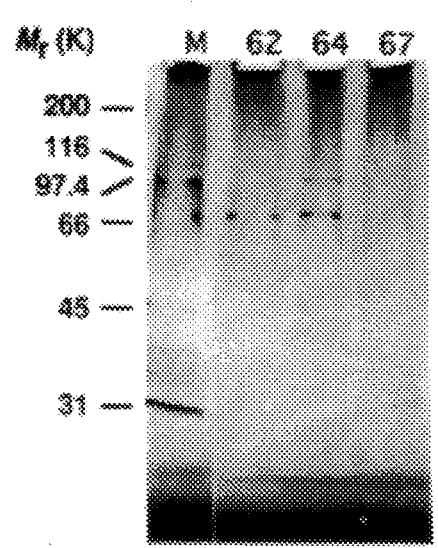

Fraction IVb was chromatographed on a 5-ml HiTrap heparin column in the same way as Fraction IVa, with the results being shown in FIG. 3 (FIGS. 3A and 3B). The active fractions eluted between 0.95–1.25 M NaCl. These fractions were combined (fraction Vb, 15 ml) and concentrated on a 1-ml HiTrap heparin column as above. 90% of the total activity which eluted between 1.07–1.17 M NaCl was combined into 3 separate pools of 3, 2, and 3 ml, respectively. Each of the pools was subjected to gel filtration as above. This resulted in fractions VIb, VIc, and VId, of 13 ml each. Fractions VIa–VId were stored at 4° C. or −80° C.

The protein compositions of fractions from the eluates resulting from gel filtration of Fractions Va, Vb, Vc, and Vd are shown in FIG. 4. In FIG. 4, 5 µl (for Va, Vb, and Vc) or 10 µl was electrophoresed on a 7.5% polyacrylamide gel and stained by silver (FIGS. 4A, 4B, 4C, and 4D).

FIG. 5A shows the gel filtration profile of Fraction Va in terms of $A_{280}$ (- - -) and enzymatic activity (- - -o- - -). FIG. 5B shows the protein composition of fractions from this gel filtration eluate, as in FIG. 4, with additional fractions shown.

The purification is summarized in Table I. Overall purification, as determined by the fraction with the highest specific activity, fraction VIa, was 3620-fold.

Sodium dodecyl sulfate-polyacrylamide gel electrophoresis (SDS-PAGE) of fraction VIa (FIGS. 4 and 5B) shows that the only significant protein component in this fraction has a molecular weight of about 110,000. This is to be compared with the apparent molecular weight on gel filtration of about 142,000 (FIG. 5A). Such discrepancies are not uncommon, and arise from molecular asymmetry of the protein. The gel filtration molecular weight indicates that the enzyme occurs as a monomer.

Heparin chromatography of fraction IVb resulted in a 12-fold purification. The protein composition of this fraction, however, remained complex (FIG. 3). Collection of the heparin eluate into three pools and application of each pool separately on a Superdex 200 gel filtration column resulted in preparations giving a protein peak in the position where pure topoisomerase V eluted (FIG. 4). In all three cases, topoisomerase activity was centered around this peak. The active fractions also contain an unknown 75,000-dalton protein (Fractions VIb and VId) or both a 75,000-dalton and an 80,000-dalton protein (Fraction VIc) along with topoisomerase V (FIG. 4). Fraction VIc, which contains as much enzymatic activity as Fraction VIa does, was purified 10-fold in the gel filtration step to about 50% purity.

Example 2

Recognition of *M. kandleri* Topoisomerase V by Antibody to Human Topoisomerase I Polyclonal antibody to human topoisomerase I binds *M. kandleri* topoisomerase V as determined by Western blotting. In FIG. 6, human topoisomerase II (Topogen, Columbus, Ohio, 10 µl, 20 units) (lane 1), λ Int protein (220 ng) (lane 2), wheat germ topoisomerase I (Promega, Madison, Wis.) (5 µl, 50 units) (lane 3), thymus topoisomerase I (United States Biochemical, Cleveland, Ohio) (5 µl, 50 units) (lane 4), human topoisomerase I (Topogen)) (5 µl, 25 units) (lane 5), and *M. kandleri* topoisomerase V (200 ng (lane 6) and 50 ng (lane 7)) were electrophoresed on a 7.5% SDS-polyacrylamide gel and blotted onto Immobilon P membrane (Millipore, Bedford, Mass.) for Western blotting. The blot was blocked with 5% dry milk in phosphate buffered saline (PBS) and probed with rabbit anti-human topoisomerase I antibody (Dr. L. Liu, Johns Hopkins University, Baltimore, Md.) diluted 1:500. Immunoreactive material was detected with [$^{125}$I] protein A (NEN, Boston, Mass.), and processed by a PhosphoImager (Molecular Dynamics, Sunnyvale, Calif.). This Western blot indicates that the antibody recognized only human topoisomerase I, wheat germ topoisomerase I and *M. kandleri* topoisomerase V. A breakdown product of human topoisomerase I, with a molecular weight of about 66,200 daltons was also recognized.

A similar Western blot was performed on individual fractions of the eluate from the gel filtration column for Fractions VIa, VIb, and VIc. (FIG. 7). In FIG. 7, 50 units of human topoisomerase I (lane 1), 2 µl of gel filtration fraction 63 from Fraction VIa (lane 2), 5 µl of gel filtration fractions 59 and 67 from Fraction VIc (lanes 3 and 4), and 5 µl of gel filtration fraction 63 from Fraction VIb (lane 5) were used. These results show that the smaller proteins occurring in Fractions VIb and VIc did not react with antibody human topoisomerase I, unlike the breakdown product of human topoisomerase I itself. This indicates that the 75,000-dalton and 80,000-dalton proteins are not breakdown products of topoisomerase V.

Example 3

Time Course and Temperature Dependence of Topoisomerase V Activity

The time course and temperature dependence of topoisomerase V activity were determined by incubating positively or negatively supercoiled pBR322 DNA with 2 ng or 20 ng topoisomerase V for various lengths of time (FIG. 8A) or at different temperatures (FIGS. 8B and 8C).

In FIG. 8A, positively supercoiled (lanes 1–5) or negatively supercoiled (lanes 6–10) pBR322 DNA was incubated with 2 ng of *M. kandleri* topoisomerase V under standard assay conditions for the indicated times. Gel electrophoresis was carried out in the presence of 1.6 µg/ml chloroquine, so that the relaxation of both positively and negatively supercoiled DNA results in the decrease of mobility of topoisomers.

In FIG. 8B, positively supercoiled pBR322 DNA was incubated with 20 ng of topoisomerase V at the indicated temperatures, and gel electrophoresis was carried out without chloroguine. Completely relaxed pBR322 DNA ("rel") during incubation at 70°–90° C. is slightly negatively supercoiled.

In FIG. 8C, negatively supercoiled pBR322 was incubated with 20 ng of topoisomerase V at the indicated temperatures, and gel electrophoresis was carried out with 25 µg/ml of chloroquine. The negatively supercoiled substrate DNA runs as slightly positively supercoiled on the gel. The product topoisomers at 94° C. had a Lk lower than the substrate DNA, while at 100° C., the products ("U") had Lk substantially less than that of substrate, the topoisomers remaining highly unwound even in the presence of 25 µg/ml of chloroquine.

The purified enzyme relaxes both positively and negatively supercoiled DNA with nearly equal proficiency. The final distribution of topoisomers does not depend on the initial supercoiling, and is not affected by a severalfold change in enzyme:DNA ratio. The relaxation activity is catalytic and processive. The rate of DNA relaxation is proportional to the quantity of enzyme added and is about 15 supercoils per minute per enzyme monomer. At 70°–90° C. the enzymatic reaction yields fully relaxed duplex DNA. At temperatures above 90° C. the enzyme produces highly unlinked forms of DNA. This effect, named unlinking, i.e., a substantial reduction in DNA linking number, is caused by DNA melting.

Example 4

Effect of Ions on Activity of Topoisomerase V

DNA topoisomerase V does not require specific ions for activity. It relaxes DNA in NaCl, KCl, and potassium glutamate. (FIGS. 9A–9D, 10A–10D). The optimum condition for relaxation is 1.55 M potassium glutamate. EDTA, and $Mg^{2+}$ do not interfere with the relaxation activity.

Figure 9A:
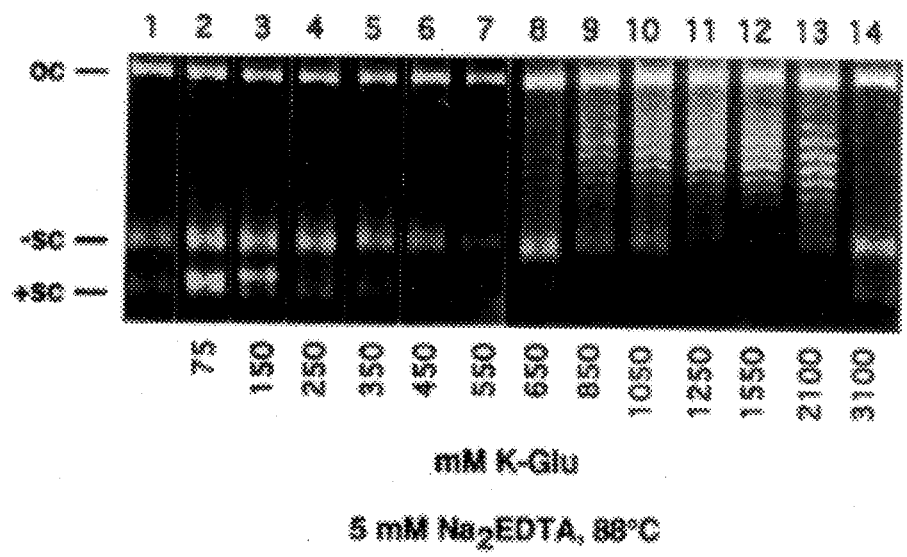
FIG. 9A is a photograph of an agarose gel showing the effect of an increasing concentration of potassium glutamate on the enzymatic activity of M. kandleri topoisomerase V with a mixture of negatively and positively supercoiled pBR322 DNA as substrate, at 88° C. in 30 mM Tris-HCl, pH 8.0 (at 25° C.), and 5 mM Na$_2$EDTA, with electrophoresis in the presence of 1.6 µg/ml chloroquine.

FIG. 9A is a photograph of an agarose gel showing the effect of an increasing concentration of potassium glutamate on the enzymatic activity of topoisomerase V (1.5 units) with a mixture of negatively and positively supercoiled pBR322 DNA (0.1 µl each form) as substrate, at 88° C. in 30 mM Tris-HCl, pH 8.0 at 25° C., and 5 mM $Na_2EDTA$. The potassium glutamate concentration is as indicated. Incubations were carried out for 15 minutes, as is the case for all other assays shown unless indicated. Electrophoresis was in the presence of 1.6 µg/ml chloroquine. Lane 1 is a control.

Figure 9B:
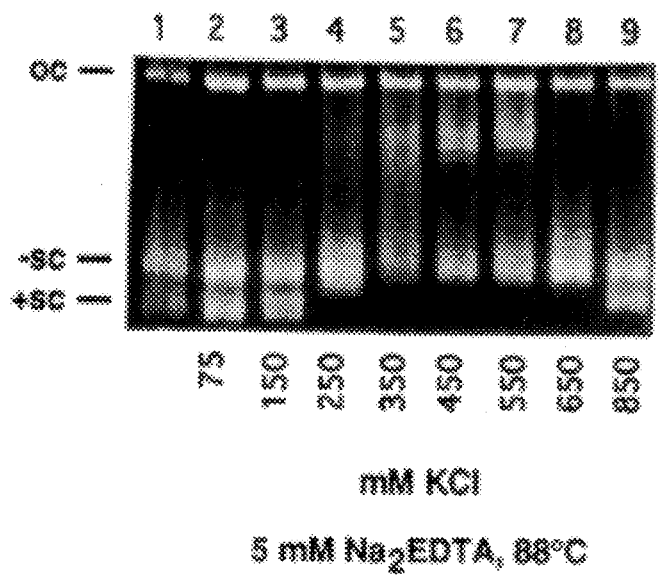
FIG. 9B is a photograph of an agarose gel showing the effect of an increasing concentration of potassium chloride on the enzymatic activity of M. kandleri topoisomerase V with a mixture of negatively and positively supercoiled pBR322 DNA as substrate, at 88° C. in 30 mM Tris-HCl, pH 8.0 (at 25° C.), 5 mM Na$_2$EDTA, with electrophoresis in the presence of 1.6 µg/ml chloroquine.

FIG. 9B is a photograph of an agarose gel showing the effect of an increasing concentration of potassium chloride on the enzymatic activity of topoisomerase V (1.5 units) with a mixture of negatively and positively supercoiled pBR322 DNA (0.1 µg each form) as substrate, at 88° C. in 30 mM Tris-HCl, pH 8.0 at 25° C., and 5 mM $Na_2EDTA$. The potassium chloride concentration is as indicated. Electrophoresis was in the presence of 1.6 µg/ml chloroquine. Lane 1 is a control.

Figure 9C:
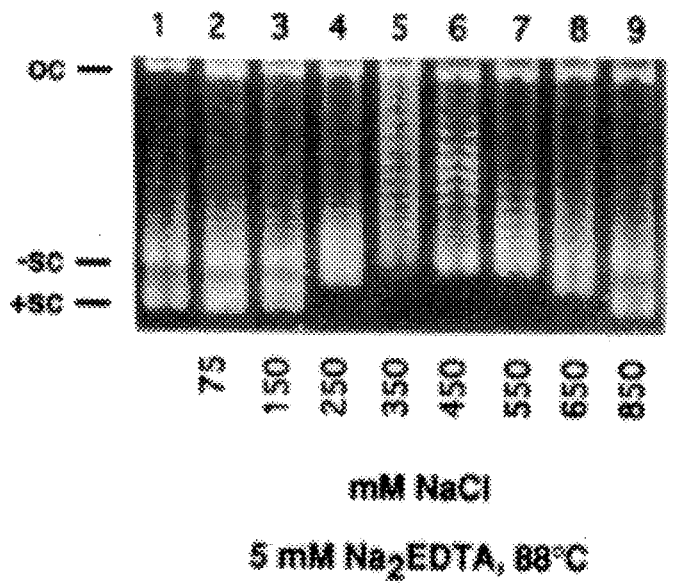
FIG. 9C is a photograph of an agarose gel showing the effect of an increasing concentration of sodium chloride on the enzymatic activity of M. kandleri topoisomerase V with a mixture of negatively and positively supercoiled pBR322 DNA as substrate, at 88° C. in 30 mM Tris-HCl, pH 8.0 (at 25° C.), 5 mM Na$_2$EDTA, with electrophoresis in the presence of 1.6 µg/ml chloroquine.

FIG. 9C is a photograph of an agarose gel showing the effect of an increasing concentration of sodium chloride on the enzymatic activity of topoisomerase V (1.5 units) with a mixture of negatively and positively supercoiled pBR322 DNA (0.1 µg each form) as substrate, at 88° C. in 30 mM Tris-HCl, pH 8.0 at 25° C., and 5 mM $Na_2EDTA$. The sodium chloride concentration was as indicated. Electrophoresis was in the presence of 1.6 µg/ml chloroquine. Lane 1 is a control.

Figure 9D:
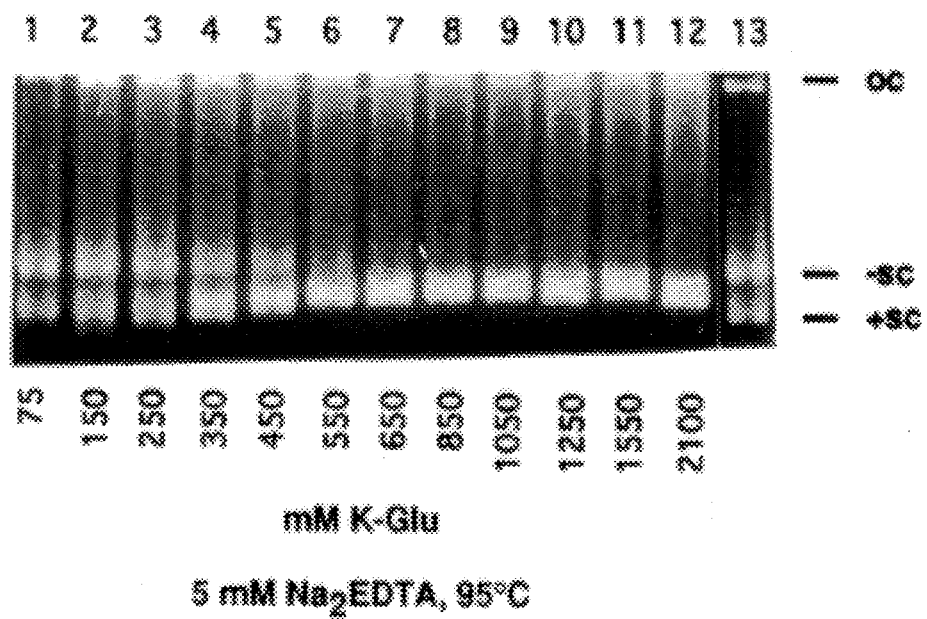
FIG. 9D is a photograph of an agarose gel showing the effect of an increasing concentration of potassium glutamate on the enzymatic activity of M. kandleri topoisomerase V with a mixture of negatively and positively supercoiled pBR322 DNA as substrate, at 95° C. in 30 mM Tris-HCl, pH 8.0 (at 25° C.), 5 mM Na$_2$EDTA, with electrophoresis in the presence of 1.6 µg/ml chloroquine.

FIG. 9D is a photograph of an agarose gel showing the effect of an increasing concentration of potassium glutamate on the degree of conversion of the initial substrate (a mixture of negatively and positively supercoiled pBR322 DNA (0.1 µg each form)) into highly unwound form of ccDNA by topoisomerase V (1.5 units) at 95° C. in 30 mM Tris-HCl, pH 8.0 at 25° C., 5 mM $Na_2EDTA$. The potassium glutamate concentration was as indicated. Lane 13 is a control.

Complete relaxation of positively supercoiled DNA and practically complete relaxation of negatively supercoiled DNA to topoisomerase V was achieved at 1.55 M potassium glutamate at 88° C.

FIGS. 10A–10D show the effect of varying ionic environments on the activity of topoisomerase V on negatively supercoiled DNA as substrate.

Figure 10A:
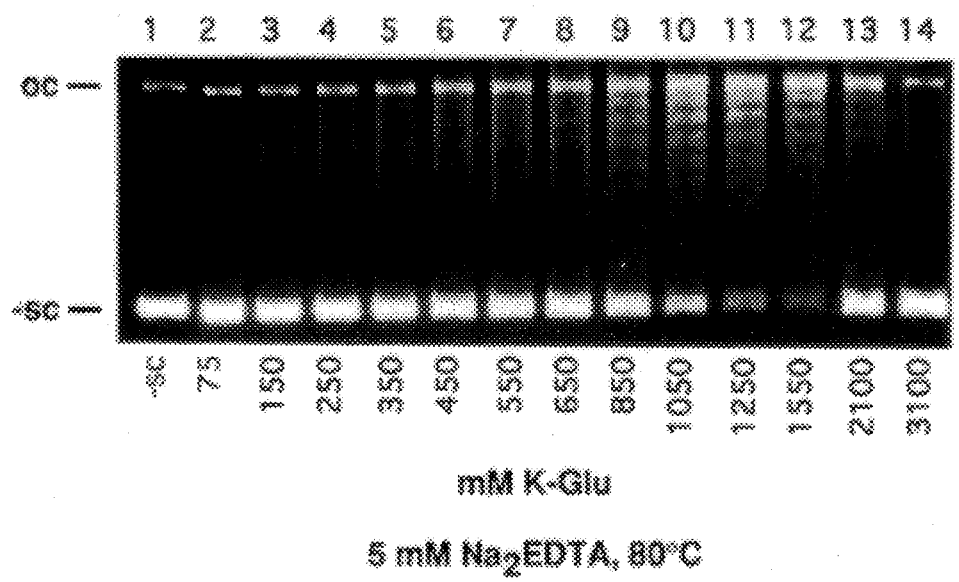
FIG. 10A is a photograph of an agarose gel showing the effect of an increasing concentration of topoisomerase V with negatively supercoiled pBR322 DNA as substrate, at 80° C. in 30 mM Tris-HCl, pH 8.0 (at 25° C.), and 5 mM Na$_2$EDTA.

FIG. 10A is a photograph of an agarose gel showing the effect of an increasing concentration of potassium glutamate on the enzymatic activity of topoisomerase V (3 units) with negatively supercoiled pBR322 DNA (0.2 µg; "-sc") as substrate, at 80° C. in 30 mM Tris-HCl, pH 8.0 at 25° C., and 5 mM $Na_2EDTA$. Lane 1 is a control. Electrophoresis was without chloroquine.

Figure 10B:
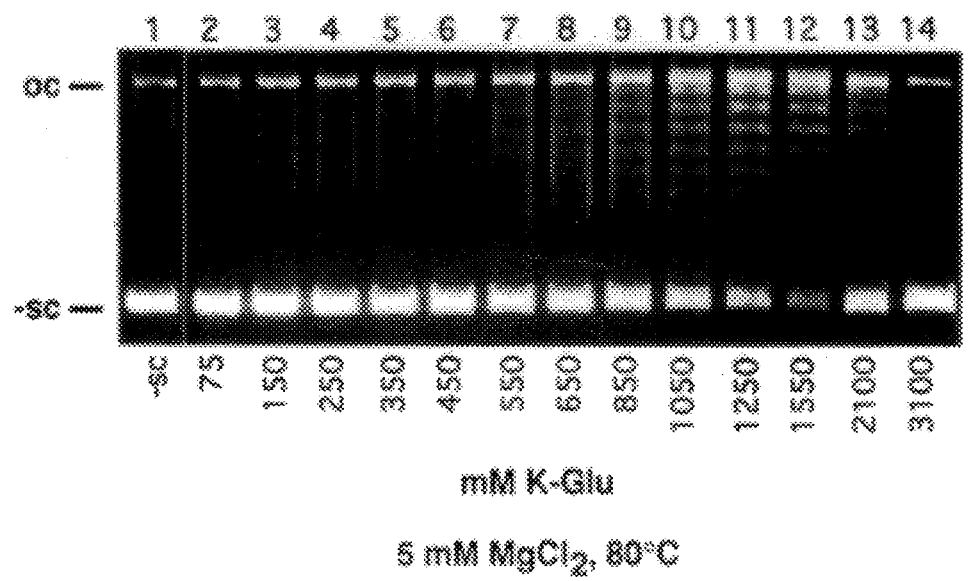
FIG. 10B is a photograph of an agarose gel as in FIG. 10A, except that 5 mM MgCl$_2$ is substituted for 5 mM Na$_2$EDTA.

FIG. 10B is a photograph of an agarose gel as in FIG. 10A, except that 5 mM $MgCl_2$ was substituted for 5 mM $Na_2EDTA$. Lane 1 is a control.

Figure 10C:
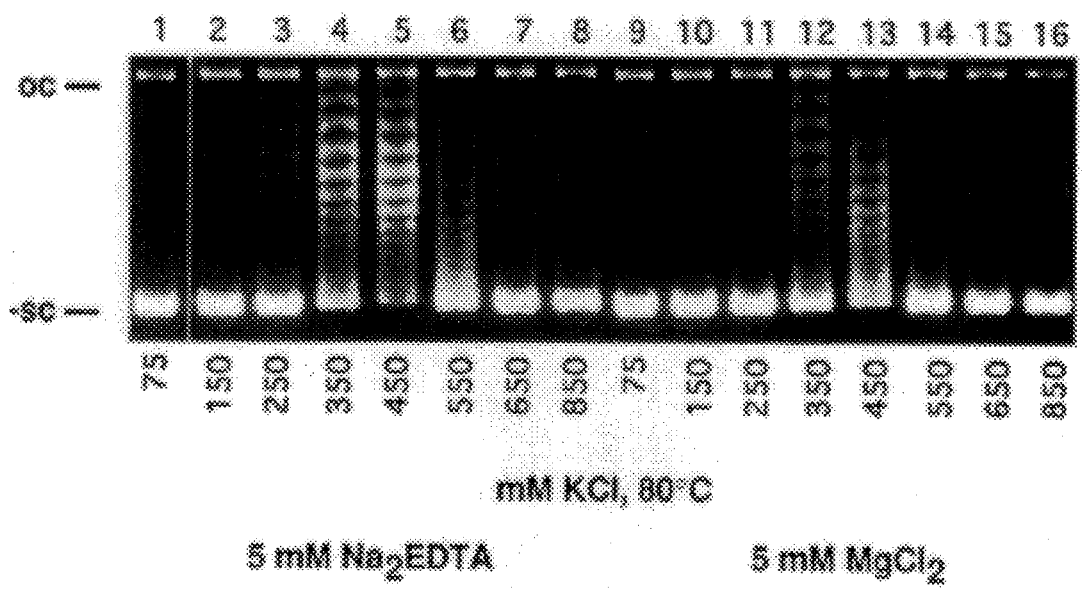
FIG. 10C is a photograph of an agarose gel showing the effect of an increasing concentration of potassium chloride on the enzymatic activity of M. kandleri topoisomerase V with negatively supercoiled pBR322 DNA as substrate, at 80° C. in 30 mM Tris-HCl, pH 8.0 (at 25° C.), and either 5 mM MgCl$_2$ or 5 mM Na$_2$EDTA.

FIG. 10C is a photograph of an agarose gel showing the effect of an increasing concentration of potassium chloride on the enzymatic activity of topoisomerase V (3 units) with negatively supercoiled pBR322 DNA (0.2 µg) as substrate, at 80° C. in 30 mM Tris-HCl, pH 8.0 at 25° C., and either 5 mM $MgCl_2$ (lanes 1–8) or 5 mM $Na_2EDTA$ (lanes 9–16).

Figure 10D:
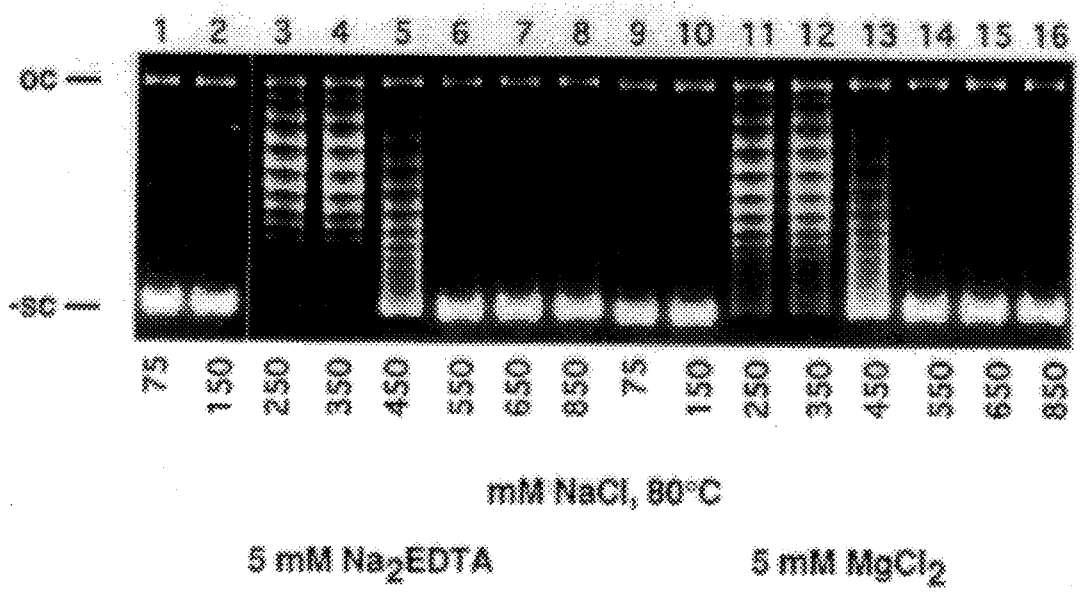
FIG. 10D is a photograph of an agarose gel showing the effect of an increasing concentration of sodium chloride on the enzymatic activity of M. kandleri topoisomerase V with negatively supercoiled pBR322 DNA as substrate, at 80° C. in 30 mM Tris-HCl, pH 8.0 (at 25° C.), and either 5 mM MgCl$_2$ or 5 mM Na$_2$EDTA.

FIG. 10D is a photograph of an agarose gel as in FIG. 10C, except that sodium chloride was substituted for potassium chloride.

These results indicate that $Cl^-$ anion substantially decreases the optimal salt concentration for DNA relaxation by topoisomerase V. Also, the use of $Na^+$ cation instead of $K^+$ decreases the optimum. There is a tendency, however, for the optimum NaCl and KCl concentrations to increase with increasing temperature.

Example 5

M. kandleri Topoisomerase V is a Type 1 Topoisomerase

M. kandleri topoisomerase V is a type 1 topoisomerase. The enzyme changes the linking number of a unique pUC19 DNA topoisomer in steps of 1 (FIG. 11).

FIG. 11 is a photograph of an agarose gel showing the relaxation of a unique topoisomer by topoisomerase V, with 0.2 µg of native pUC19 DNA (lanes 1 and 2) or its unique topoisomer (lanes 3 and 4) as substrate and 15 units of enzyme (lanes 2 and 4), with electrophoresis in the presence of 2 µg/ml of chloroquine.

The results of FIG. 11 indicate that a number of topoisomers are detectable as a result of the action of topoisomerase V on a unique negatively supercoiled topoisomer of pUC19 DNA. The Lk of the produced topoisomers increases in steps of 1.

Example 6

Single-Stranded DNA Does Not Affect the Relaxation of Negatively or Positively Supercoiled DNA by *M. kandleri* Topoisomerase V Single-stranded φX174 DNA does not affect the relaxation of negatively or positively supercoiled pBR322 DNA by topoisomerase V at 70° C. and 90° C. at any φX:pBR 322 ratio up to 4.9 (FIG. 12).

Figure 12A:
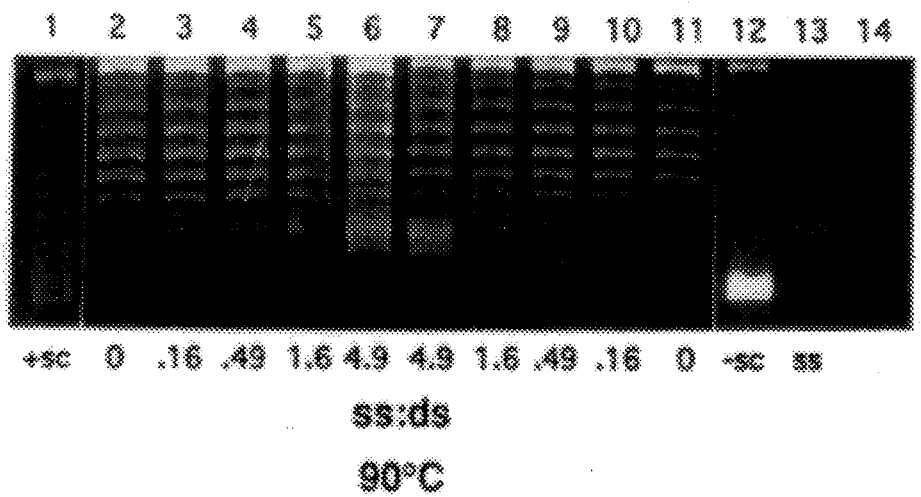
FIG. 12A and 12B is a photograph of an agarose gel showing the effect of an increasing concentration of single-stranded φX174 DNA on the relaxation of positively or negatively supercoiled pBR322 DNA by M. kandleri topoisomerase V at 90° C. or 70° C.
Figure 12B:
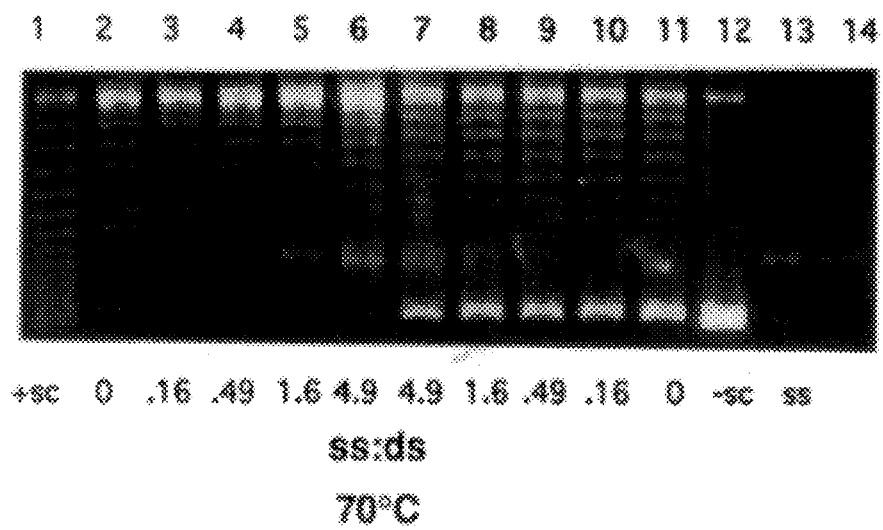

FIG. 12 is a photograph of an agarose gel showing the effect of an increasing concentration of single-stranded φX174 DNA on the relaxation of positively (0.2 µg; lanes 2–6) or negatively (0.2 µg; lanes 7–11) supercoiled pBR322 DNA by topoisomerase V (5 units) at 90° C. (panel A; FIG. 12A) or 70° C. (panel B; FIG. 12B). Controls were positively supercoiled pBR322 DNA (lane 1), negatively supercoiled pBR322 DNA (lane 12), single-stranded φX174 DNA before incubation (lane 13), and single-stranded φX174 DNA after incubation (lane 14).

This data suggests that topoisomerase V enzyme does not form an irreversible complex between the enzyme and short duplex regions of single-stranded φX174 DNA, unlike mesophilic eukaryotic topoisomerase I enzymes, which are inhibited by short duplex regions formed in single-stranded φX174 DNA. These results also indicate that topoisomerase V requires double-stranded regions of DNA for binding and topoisomerization.

Example 7

Unlinking Activity of Topoisomerase V

Topoisomerase V from *M. kandleri* catalyzes an unlinking reaction; that is, a reaction which decreases Lk of closed circular DNA below its initial value. This is indicative of at least partial unwinding of the Watson-Crick double helical structure. Unlinking activity is favored at higher temperature: the higher the temperature, the more unwound DNA is generated (FIGS. 8B,C)

The unlinking activity of topoisomerase V is most clearly demonstrated by activity on relaxed DNA (FIGS. 13A–13D). This is because the products are clearly distinguishable from the substrate on gel electrophoresis, as the unlinking causes an increased mobility of the relaxed DNA.

Figure 13A:
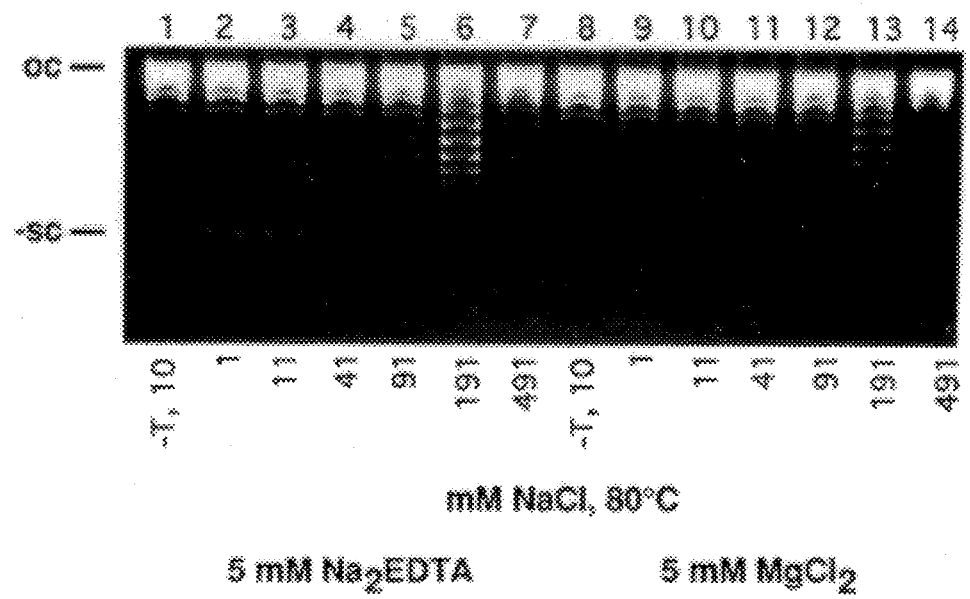
FIG. 13A is a photograph of an agarose gel showing the effect of an increasing concentration of sodium chloride on the activity of M. kandleri topoisomerase on relaxed pBR322 DNA at 80° C. in the presence of 5 mM Na$_2$EDTA or 5 mM MgCl$_2$, demonstrating the unlinking activity of the enzyme.

FIG. 13A is a photograph of an agarose gel showing the effect of an increasing concentration of sodium chloride on the activity of topoisomerase V (2 units) on relaxed pBR322 DNA (0.2 µg) at 80° C. in the presence of 5 mM $Na_2EDTA$ (lanes 2–7) or 5 mM $MgCl_2$ (lanes 9–14). Lanes 1 and 8 contained no enzyme.

Figure 13B:
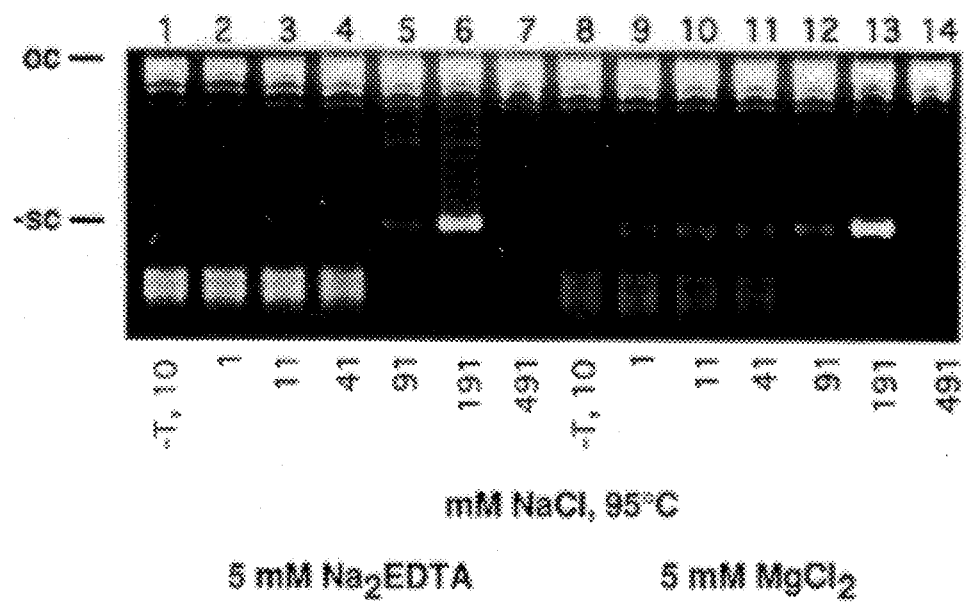
FIG. 13B is a photograph of an agarose gel showing the effect of an increasing concentration of sodium chloride on the activity of M. kandleri topoisomerase on relaxed pBR322 DNA at 95° C. in the presence of 5 mM Na$_2$EDTA or 5 mM MgCl$_2$, demonstrating the unlinking activity of the enzyme.

FIG. 13B is a photograph of an agarose gel as in FIG. 13A, but with the enzymatic reaction having been performed at 95° C.

Figure 13C:
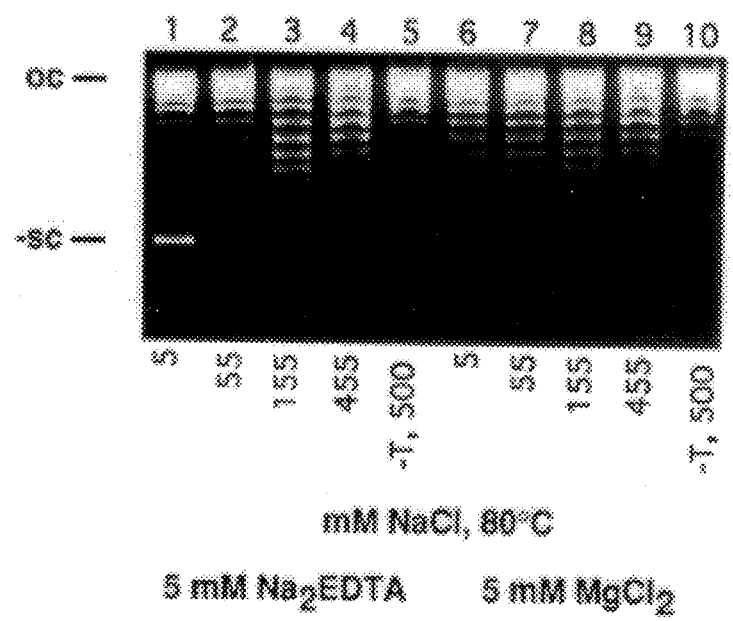
FIG. 13C is a photograph of an agarose gel showing the effect of an increasing concentration of sodium chloride on the unlinking activity of M. kandleri topoisomerase on relaxed pBR322 DNA at 80° C. in the presence of 5 mM Na$_2$EDTA or 5 mM MgCl$_2$, at higher concentrations of sodium chloride.

FIG. 13C is a photograph of an agarose gel as in FIG. 13A, but at higher concentrations of sodium chloride and with a greater quantity (10 units) of enzyme. Lanes 5 and 10 contain no enzyme. Lanes 1–5 contain 5 mM $Na_2EDTA$; lanes 6–10 contain 5 mM $MgCl_2$.

Figure 13D:
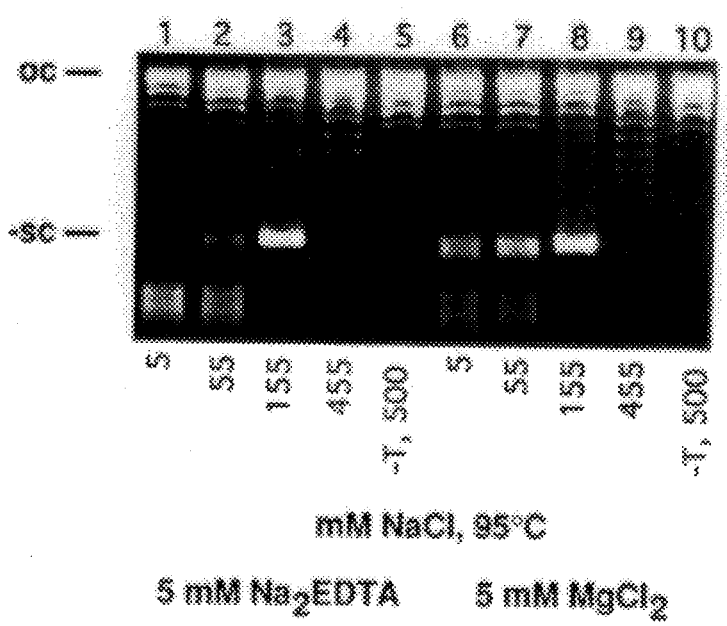
FIG. 13D is a photograph of an agarose gel showing the effect of an increasing concentration of sodium chloride on the unlinking activity of *M. kandleri* topoisomerase on relaxed pBR322 DNA at 95° C. in the presence of 5 mM Na$_2$EDTA or 5 mM MgCl$_2$, at higher concentrations of sodium chloride.

FIG. 13D is a photograph of an agarose gel as in FIG. 13C, but with the enzymatic reaction having been performed at 95° C.

At 75 and 150 mM of monovalent cation, the products of the unlinking reaction can be seen as the band between +sc and −sc bands in FIGS. 9A, 9B, and 9C in lanes 2 and 3. At constant temperature, an increase in ionic strength of the reaction mixture results in a switch from the unlinking mode to the relaxation mode of activity.

Topoisomerase V retains its unlinking activity at NaCl concentrations as low as 1 mM. The lower the ionic strength, the lower the temperature at which unlinking occurs (FIG. 13A, lane 2; FIG. 13B, lane 9). When the unlinking reaction is performed at 95° C., intermediate topoisomers are seen at 155 and 191 mM NaCl and are absent at salt concentrations from 1 mM NaCl to 91 mM NaCl (FIGS. 13B, 13D). This suggests the unlinking of relaxed DNA is processive at low salt concentrations and tends to be distributive at high salt concentrations.

Example 8

Reversibility of *M. kandleri* Topoisomerase V Binding to DNA

At high ionic strengths, topoisomerase V readily dissociates from one DNA molecule and binds another, acting on both DNA molecules. However, at lower ionic strength, topoisomerase V is tightly bound to the DNA molecule to which it binds first and disassociation and binding to another DNA molecule is inefficient. These results are shown in FIGS. 14A and 14B.

In these experiments, topoisomerase V was preincubated with substrate DNA at high salt (300 mM NaCl). Then the sample was diluted and the NaCl concentration was adjusted either to 300 mM NaCl or low salt (50 mM). Competitor DNA was then added. The enzymatic reaction was performed at 90° C. and the results were analyzed by two-dimensional gel electrophoresis.

FIG. 14A is a photograph of an two-dimensional agarose gel showing competition of topoisomerase V (100 units) for substrate DNA with relaxed pBR322 DNA and relaxed pGEM3 DNA, the electrophoresis being done without chloroquine in the first dimension and with 4 µg/ml chloroquine in the second dimension. Lanes 1–3 involved initial incubation at 300 mM NaCl with one of the two DNAs, followed by adjustment of NaCl concentration to 50 mM and addition of the competitor DNA. After raising the temperature to 90° C., incubation was for 15 minutes. In lanes 6–8, NaCl concentration remained at 300 mM. In lanes 1 and 6, both 0.2 µg relaxed pBR322 DNA and 0.2 µg relaxed pGEM3 DNA were present at the start of incubation. In lanes 2 and 7, 0.2 µg relaxed pBR322 DNA was present at the start of incubation, and 0.2 µg pGEM3 DNA was added after dilution or reduction of NaCl concentration. In lanes 3 and 8, 0.2 µg relaxed pGEM3 DNA was present at the start of incubation, and 0.2 µg pBR322 DNA was added after dilution or reduction of NaCl concentration. Lane 4 contained relaxed pGEM3, lane 5 relaxed pBR322, lane 9 negatively supercoiled pGEM3, and lane 10, negatively supercoiled pBR322 DNA.

FIG. 14B is similar to FIG. 14A except that the composite preparation of pGEM3 contained supercoiled and relaxed pGEM3 was used, and incubation at 90° C. was for 10 minutes.

Irrespective of whether the substrate was pBR322 DNA and the competitor was pGEM3 or vice-versa, whether both substrate and competitor were relaxed, the substrate was relaxed and the competitor was supercoiled, or vice-versa, in all cases at 300 mM NaCl the enzyme unlinked both substrate and competitor DNA (FIGS. 14A, 14B). This means that at this salt concentration topoisomerase freely disassociates and binds DNA. However, if the NaCl concentration was adjusted to 50 mM before competitor DNA was added, the degree of reaction on the competitor DNA was very low.

Example 9

Inhibitors of Topoisomerase V

Camptothecin is not as potent an inhibitor of *M. kandleri* topoisomerase V as of many eukaryotic topoisomerase I species. Camptothecin is soluble in dimethyl sulfoxide, an organic solvent that does not inhibit eukaryotic topoisomerases. However, dimethyl sulfoxide alone, without camptothecin, inhibits *M. kandleri* topoisomerase V (FIG. 15).

FIG. 15 is a photograph of an agarose gel showing the effect of dimethyl sulfoxide and camptothecin on the activity of topoisomerase V (15 units) with 0.2 µg pBR322 DNA as substrate at 70° C. The indicated concentrations of dimethyl sulfoxide (DMSO) and camptothecin (CPT) were used. Incubations were carried out for 15 minutes.

Example 10

Covalent Complex Formation Between Topoisomerase V and DNA

Figure 16:
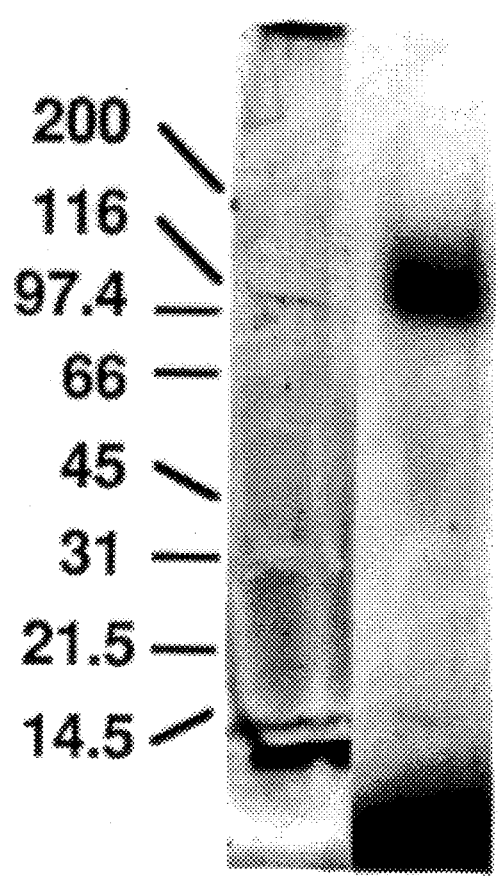
FIG. 16 is a photograph of a silver-stained 4–15% gradient polyacrylamide gel and its autoradiograph showing covalent complex formation between pBR322 DNA and *M. kandleri* topoisomerase V.

*M. kandleri* topoisomerase V forms a covalent complex with DNA. This is demonstrated in FIG. 16. Uniformly labeled pBR322 DNA was prepared with the T7 QuickPrime kit (Pharmacia) and [α-$^{32}$P] dCTP (NEN). Labeled DNA (5 ng) was incubated with 40 ng of topoisomerase V in 20 mM Tris-HCl, pH 8.0, 0.1 M NaCl at 70° C. for three minutes. Then KOH was added to 0.05 N and incubation was continued for one minute. The mixture was neutralized by Tris-HCl and magnesium acetate was added to 10 mM. The DNA was digested by 20 units of DNase I and 300 units of exonuclease III (Pharmacia) at 37° C. for 50 minutes. The products were analyzed by SDS-PAGE on a 4–15% gradient gel. The silver-stained gel (lane 1) and its autoradiograph (lane 2) are shown (FIG. 16). These results show that DNA forms a covalent complex with topoisomerase V.

Example 11

DNA Cleavage by *M. kandleri* Topoisomerase V

Figure 17:
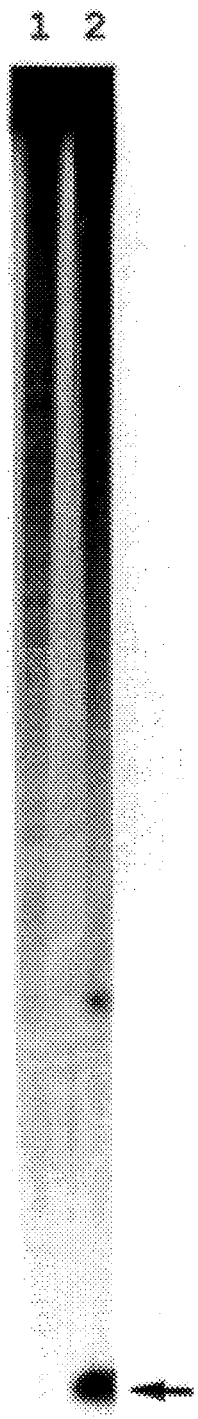
FIG. 17 is an autoradiograph of a denaturing 6% polyacrylamide gel showing pGEM1 DNA cleaved by *M. kandleri* topoisomerase V, indicating the site of cleavage.

As indicated above (Example 5; FIG. 11), topoisomerase V is a type 1 topoisomerase that makes cuts in one strand at a time. The exact site of cleavage was determined as shown in FIG. 17. pGEM1 DNA (Promega) was cut with Hind III restriction endonuclease and the 3'-end was filled in with [α-$^{32}$P] dCTP and unlabeled deoxyribonucleoside triphosphates by the Klenow fragment of *Escherichia coli* DNA polymerase I, followed by digestion with Nae I restriction endonuclease. The 280-bp end-labeled fragment was gel purified and incubated with (FIG. 17, lane 2) or without (FIG. 17, lane 1) topoisomerase V. The samples were boiled in running buffer (6 M urea, 0.5× TBE) and analyzed using denaturing 6% polyacrylamide gel electrophoresis. The major cleavage site is shown by an arrow.

The exact position of the major topoisomerase V cleavage site on the 280-bp fragment of pGEM 1 DNA was determined by comparing the mobility of the cleavage product with the Maxam-Gilbert sequencing ladder. The sequence is shown in FIG. 18. The sequence is similar, though not identical, to the strongest cleavage sites for eukaryotic topoisomerases I (B. J. Bonven et al. *Cell* 41:541–551 (1985)).

Example 12

Isolation of Covalent Complex Between *M. kandleri* Topoisomerase V and Open Circular DNA Covalent complexes between *M. kandleri* topoisomerase V enzyme were isolated for three different plasmids: pHOT1 containing the consensus cleavage site for eukaryotic topoisomerase I inserted in the pUC12 vector, pGEM3, and pBR322. Relaxed DNA (0.2 µg for each plasmid) was incubated in 30 mM Tris-HCl, pH 8.0 at 25° C., 300 mM NaCl, 5 mM magnesium acetate with or without topoisomerase V (100 units) at 90° C. for 3 minutes. Sodium dodecyl sulfate was added to 1% and the resulting mixtures were incubated for 90° C. for 1 minute. A similar reaction was performed using supercoiled DNA for each plasmid and human topoisomerase I with NaCl at 85 mM. For each assay condition (i.e., each plasmid, relaxed or supercoiled, with or without *M. kandleri* topoisomerase V or human topoisomerase I), an aliquot was digested with 2 µg proteinase K at 42° C. for 4 hours.

Two-dimensional 1.5% agarose gel electrophoresis was performed in TAE buffer with 0.1% SDS in the first dimension and with 4 µg/ml chloroquine in the second dimension.

The results are shown in FIG. 19 for each of the three plasmids (pHOT1, top; pGEM3, center; pBR322 (bottom)). For each plasmid, the lanes shown are as follows: lane 1, untreated supercoiled DNA; lane 2, relaxed DNA incubated with *M. kandleri* topoisomerase V; lane 3, relaxed DNA incubated with *M. kandleri* topoisomerase V and digested with proteinase K; lane 4, relaxed DNA without *M. kandleri* topoisomerase V; lane 5, relaxed DNA without *M. kandleri* topoisomerase V and digested with proteinase K; lane 6, untreated relaxed DNA; lane 7, supercoiled DNA incubated with human topoisomerase I; lane 8, supercoiled DNA incubated with human topoisomerase I and digested with proteinase K; lane 9, supercoiled DNA without human topoisomerase I; and lane 10, supercoiled DNA without human topoisomerase I and digested with proteinase K. Lane 1 also contained 1 µg pGEM3 DNA.

Lane 2 for all three plasmids tested shows that the incubation converts relaxed DNA to a highly unwound form. In addition, a band (indicated by an arrow) above open circular DNA appears. Lane 3 shows that this product is sensitive to proteinase K, which indicates that it is a covalent complex of *M. kandleri* topoisomerase V with circular DNA fixed by the protein denaturant. Proteinase K digests topoisomerase and yields a nicked circle of DNA with one or a few amino acids attached to the DNA, which co-migrates with open circular DNA.

Only about 1% of the enzyme molecules were trapped. There was no substantial difference among the three substrate DNAs used in the yield of the complexes, even though pHOT1 has the consensus site for topoisomerase I and pGEM3 and pBR322 lack the site.

For comparison, covalent complex formation by human topoisomerase V is also shown (lanes 7 and 8). The results are similar to those obtained with *M. kandleri* topoisomerase V.

Example 13

Proteolytic Fragments of the *M. kandleri* Topoisomerase V

Figure 20:
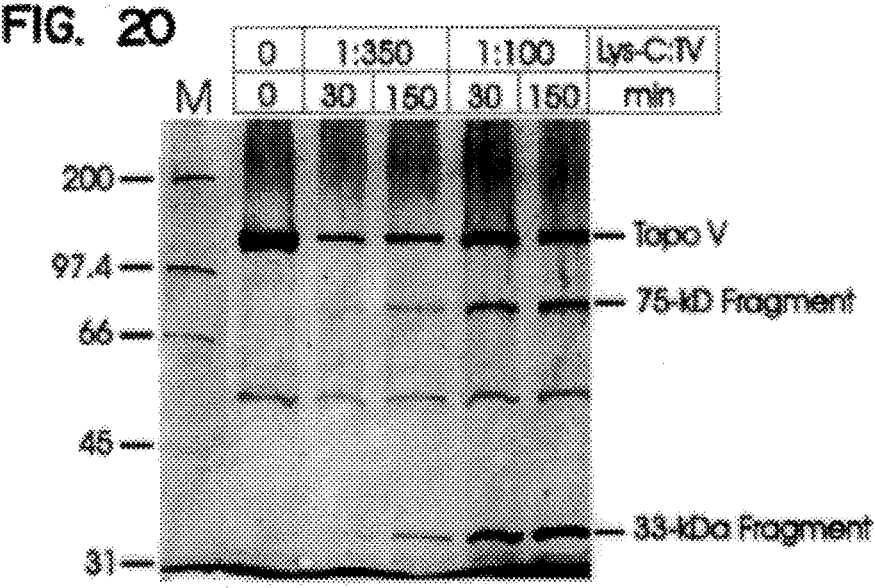
FIG. 20 is a photograph of a silver-stained 7.5% polyacrylamide gel of topoisomerase V fragments produced by the endoproteinase Lys-C under native conditions.

Treatment of the *M. kandleri* topoisomerase V with endoproteinase Lys-C, a protease that cleaves at the carboxylic side of lysine (K), generates two large fragments which are relatively stable to further digestion (FIG. 20)

Samples of topoisomerase V (10 µg/ml and 35 µg/ml) were incubated with 0.1 µg/ml Lys-C (Promega, Madison, Wis.) in 30 mM sodium phosphate, pH 8.0, 0.5 M NaCl, 10 mM β-mercaptoethanol for 30 and 150 min at 37° C. Reactions were terminated by adding 1 mM TLCK. Fractions were analyzed by SDS-PAGE (7.5%) and stained by silver.

For large-scale proteolysis, about 100 μg of topoisomerase V was digested with 3 μg of Lys-C in the above buffer for 3 h. Fragments were separated by 6% SDS-PAGE and blotted onto Immobilon P membrane (Millipore, Bedford, Mass.).

FIG. 20 shows that molecular masses of the fragments are about 75 kD and 33 kD. Determination of the N-terminal sequences of these fragments showed that they are derived from the N terminus (75-kD fragment) and from the C terminus (33-kD fragment) of topoisomerase V. The 33-kD fragment, designated as Fragment IV, has the following N-terminal amino acid sequence: Lys-Ser-Gly-Arg-Gln-Glu-Arg-Ser-Glu-Glu-Glu-Trp-Lys-Glu-Trp-Leu-Glu-Arg-Lys-Val-Gly-Glu-Gly-Arg-Ala-Arg-Arg-Leu-Ile-Glu-Tyr-Phe-Gly-Ser-Ala (SEQ ID NO: 1).

Figure 21:
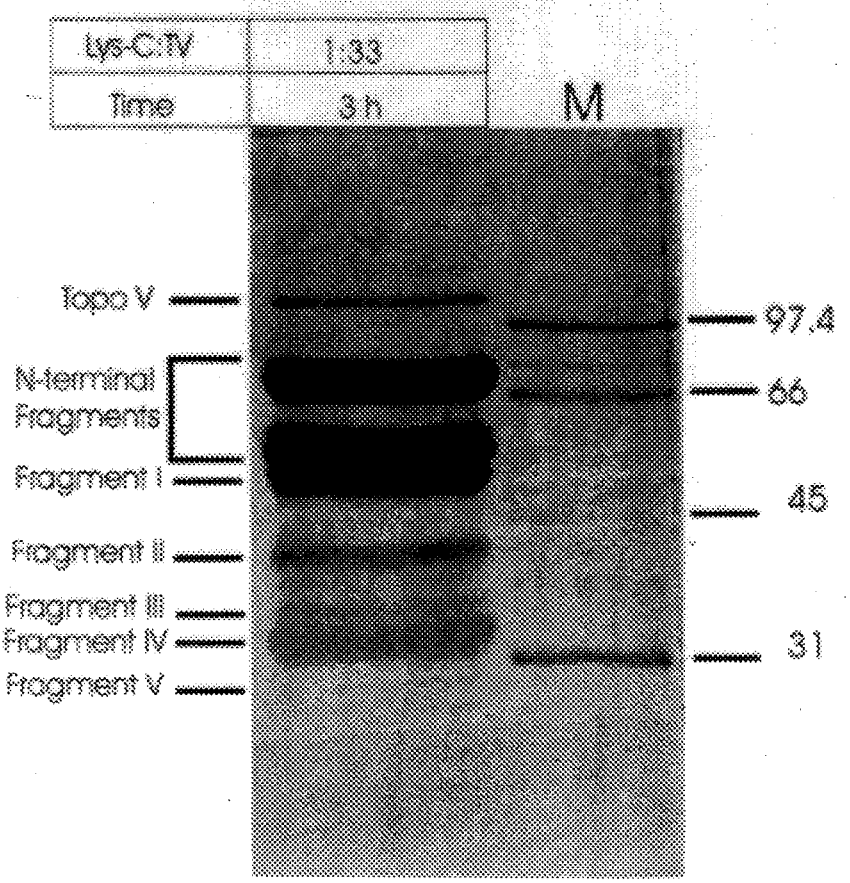
FIG. 21 is a photograph of a Coomassie blue-stained immunoblot of topoisomerase V fragments produced by the endoproteinase Lys-C under conditions of partial proteolysis and which have been used for protein microsequencing.

The fragments were found to be resistant to further digestion under the conditions of FIG. 20 and could represent structural and/or functional domains within *M. kandleri* topoisomerase V However, prolonged incubation and increased Lys-C:topoisomerase V ratio leads to appearance of a number of additional fragments (FIG. 21), including a N-terminal fragment of about 55,000 daltons.

ADVANTAGES OF THE INVENTION

Thermostable topoisomerase V from Methanopyrus kandleri can function over a broad range of temperatures and ionic conditions to promote both relaxation of supercoils and unlinking of ccDNA. The enzyme has many applications in enzymatic DNA sequencing, in gene cloning, in nucleic acid amplification by the PCR or LCR techniques, and in hybridization probe preparation, i.e., in any procedure that requires denaturing of ccDNA or annealing of primers or hybridization probes.

Although the present invention has been described in considerable detail with regard to certain preferred versions thereof, other versions are possible. Therefore, the spirit and scope of the appended claims should not be limited to the description of the preferred version contained herein.

What is claimed is:

1. A substantially purified thermostable type 1-group B DNA topoisomerase not requiring magnesium for its activity that relaxes both negatively and positively supercoiled DNA, cleaves DNA at the third adenosine residue in the sequence A-C-A-C-T-A-T-A-G-A-A-T-A-C-A-A-G (SEQ ID NO: 4), and makes a covalent complex with the 3'-phosphoryl terminus of the cleaved DNA, the topoisomerase substantially free of other enzymes acting on DNA, the topoisomerase possessing an amino-terminal amino acid sequence
of Ala-Leu-Val-Tyr-Asp-Ala-Glu-Phe-Val-Gly-Ser-Glu-Arg-Glu-Phe-Glu-Glu-Glu-Arg-Glu-Thr-Phe-Leu-Lys-Gly-Val-Lys-Ala-Tyr-Asp-Gly-Val-Leu-Ala-Thr-Arg-Tyr-Arg-Tyr-Arg-Tyr-Leu-Met-Glu-Arg-Ser-Ser-Ser-Ala (SEQ ID NO: 3).

2. A substantially purified thermostable type 1-group DNA topoisomerase of thermophilic prokaryotic origin active at a temperature of at least 50° C., the topoisomerase substantially free of other enzymes acting on DNA, the topoisomerase possessing at least one amino acid sequence of *Methanopyrus kandleri* topoisomerase V selected from the group consisting of:

(a) the sequence Lys-Ser-Gly-Arg-Gln-Glu-Arg-Ser-Glu-Glu-Glu-Trp-Lys-Glu-Trp-Leu-Glu-Arg-Lys-Val-Gly-Glu-Gly-Arg-Ala-Arg-Arg-Leu-Ile-Glu-Tyr-Phe-Gly-Ser-Ala (SEQ ID NO: 1); and (b) the sequence Lys-Tyr-Gly-Ser-Ala-Ser-Ala-Val-Arg-Arg-Leu-Pro-Val-Glu-Glu-Leu-Arg-Glu-Leu-Gly-Phe-Ser-Asp-Asp-Glu (SEQ ID NO: 2); the topoisomerase being magnesium independent, relaxing both negatively and positively supercoiled DNA, making a covalent complex with the 3'-end of the broken DNA strand, and cleaving DNA at the third adenosine residue in the sequence A-C-A-C-T-A-T-A-G-A-A-T-A-C-A-A-G (SEQ ID NO: 4).

3. A method of relaxing supercoiled DNA comprising treating a supercoiled DNA selected from the group consisting of positively supercoiled DNA and negatively supercoiled DNA with the topoisomerase of claim 1 at a temperature and ionic conditions at which the separation of complementary strands of the linear form of treated closed circular DNA does not occur and at a temperature and ionic conditions that allow the enzyme to bind to DNA and catalyze the relaxation reaction to produce relaxed DNA.

4. A method of relaxing supercoiled DNA comprising treating a supercoiled DNA selected from the group consisting of positively supercoiled DNA and negatively supercoiled DNA with the topoisomerase of claim 2, at a temperature and ionic conditions at which the separation of complementary strands of the linear form of treated closed circular DNA does not occur and at a temperature and ionic conditions that allow the enzyme to bind to DNA and catalyze the relaxation reaction to produce relaxed DNA.

5. A method of unlinking closed circular DNA comprising treating closed circular DNA with the topoisomerase of claim 1 at a temperature and ionic conditions allowing separation of complementary DNA strands of the linear form of treated closed circular DNA and at a temperature and ionic conditions that allow the enzyme to bind to DNA and catalyze the unlinking reaction to produce DNA with a linking number lower than the linking number of the DNA before treatment.

6. A method of unlinking closed circular DNA comprising treating closed circular DNA with the topoisomerase of claim 2 at a temperature and ionic conditions allowing separation of complementary DNA strands of the linear form of treated closed circular DNA and at a temperature and ionic conditions that allow the enzyme to bind to DNA and catalyze the unlinking reaction to produce DNA with a linking number lower than the linking number of the DNA before treatment.

* * * * *

UNITED STATES PATENT AND TRADEMARK OFFICE
CERTIFICATE OF CORRECTION

PATENT NO. : 5,656,463

DATED : August 12, 1997

INVENTOR(S) : Slesarev

It is certified that error appears in the above-identified patent and that said Letters Patent is hereby corrected as shown below:

Abstract, line 13, insert --of-- after the word "capable"

Column 2, line 53, "Boutbier" should read --Bouthier--

Column 3, line 29, "clearable" should read --cleavable--

Column 8, line 8, "kadleri" should read --kandleri--

Column 8, line 9, insert --is-- after the letter "V"

Column 8, line 24, "pro" should read --Pro--

Column 8, line 47, "and/Or" should read --and/or--

Column 10, line 19, insert --potassium glutamate on the enzymatic activity of M.kandleri-- after the word "of" (second occurrence).

Columns 17 & 18, line 3, (Footnote) "amylalyticus" should read --amylolyticus--

Column 25, line 8, "chloroguine" should read --chloroquine--

Column 35, (cl-1), line 15, delete "Arg-Tyr" after the words "Tyr-Arg-Tyr"

UNITED STATES PATENT AND TRADEMARK OFFICE
CERTIFICATE OF CORRECTION

PATENT NO. : 5,656,463
DATED : August 12, 1997
INVENTOR(S) : Slesarev

It is certified that error appears in the above-identified patent and that said Letters Patent is hereby corrected as shown below:

Column 8, line 12, delete "is".

Signed and Sealed this

Seventeenth Day of March, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Methanopyrus kandleri ( x i ) SEQUENCE DESCRIPTION: SEQ ID NO:1:

```
Lys  Ser  Gly  Arg  Gln  Glu  Arg  Ser  Glu  Glu  Glu  Trp  Lys  Glu  Trp  Leu
 1                   5                        10                      15
Glu  Arg  Lys  Val  Gly  Glu  Gly  Arg  Ala  Arg  Arg  Leu  Ile  Glu  Tyr  Phe
               20                       25                      30
Gly  Ser  Ala
           35
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Methanopyrus kandleri ( x i ) SEQUENCE DESCRIPTION: SEQ ID NO:2:

Lys Tyr Gly Ser Ala Ser Ala Val Arg Arg Leu Pro Val Glu Glu Leu
1               5                   10                  15

Arg Glu Leu Gly Phe Ser Asp Asp Glu
            20              25

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Methanopyrus kandleri ( x i ) SEQUENCE DESCRIPTION: SEQ ID NO:3:

Ala Leu Val Tyr Asp Ala Glu Phe Val Gly Ser Glu Arg Glu Phe Glu
1               5                   10                  15

Glu Glu Arg Glu Thr Phe Leu Lys Gly Val Lys Ala Tyr Asp Gly Val
            20                  25                  30

Leu Ala Thr Arg Tyr Leu Met Glu Arg Ser Ser Ser Ala
            35              40                  45

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: plasmid pBR322

( x i ) SEQUENCE DESCRIPTION: SEQ ID NO:4:

ACACTATAGA ATACAAG                                             17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
        ( A ) ORGANISM: Consensus topoisomerase V sequence ( x i ) SEQUENCE DESCRIPTION: SEQ ID NO:5:

AGACTTNAGA RAAAWWW                                            17